US007737139B2

(12) United States Patent
Allegretti et al.

(10) Patent No.: US 7,737,139 B2
(45) Date of Patent: Jun. 15, 2010

(54) SULFONIC ACIDS, THEIR DERIVATIVES AND PHARMACEUTICAL COMPOSITIONS CONTAINING THEM

(75) Inventors: Marcello Allegretti, L'Aquila (IT); Andrea Aramini, L'Aquila (IT); Maria Candida Cesta, L'Aquila (IT); Riccardo Bertini, L'Aquila (IT); Cinzia Bizzarri, L'Aquila (IT); Francesco Colotta, L'Aquila (IT)

(73) Assignee: Dompe PHA.R.MA S.p.A., L'Aquila (IT)

( * ) Notice: Subject to any disclaimer, the term of this patent is extended or adjusted under 35 U.S.C. 154(b) by 971 days.

(21) Appl. No.: 10/544,396

(22) PCT Filed: Mar. 11, 2004

(86) PCT No.: PCT/EP2004/050293

§ 371 (c)(1),
(2), (4) Date: May 18, 2006

(87) PCT Pub. No.: WO2004/080951

PCT Pub. Date: Sep. 23, 2004

(65) Prior Publication Data

US 2006/0258730 A1 Nov. 16, 2006

(30) Foreign Application Priority Data

Mar. 14, 2003 (EP) .................................. 03005783

(51) Int. Cl.
*A61K 31/5375* (2006.01)
*A61K 31/40* (2006.01)
*C07D 207/30* (2006.01)
*C07D 265/30* (2006.01)

(52) U.S. Cl. ..................... 514/231.2; 544/106; 544/358; 546/184; 548/530; 548/540; 514/408; 514/423

(58) Field of Classification Search ................. 548/530, 548/540; 514/408, 423, 231.2; 564/305; 546/184; 544/106, 358
See application file for complete search history.

(56) References Cited

U.S. PATENT DOCUMENTS

| 5,216,026 | A | * | 6/1993 | Howbert ..................... 514/592 |
| 5,886,044 | A | * | 3/1999 | Widdowson et al. ........ 514/596 |
| 6,069,172 | A |   | 5/2000 | Bertini et al. |
| 6,147,115 | A | * | 11/2000 | Crowell et al. .............. 514/592 |
| 6,262,113 | B1 | * | 7/2001 | Widdowson et al. ........ 514/522 |
| 6,348,032 | B1 | * | 2/2002 | Sperl et al. .................. 514/338 |
| 6,410,584 | B1 | * | 6/2002 | Pamukcu et al. ............. 514/416 |
| 6,774,212 | B2 | * | 8/2004 | Han ............................ 530/331 |
| 7,115,647 | B2 | * | 10/2006 | Pamukcu et al. ............ 514/416 |

FOREIGN PATENT DOCUMENTS

DE 1949987 A1 4/1970

| DE | 2428223 | A1 | 1/1975 |
| DE | 3128676 | A1 | 4/1982 |
| GB | 1283943 | A | 8/1972 |
| GB | 2080797 | A | 2/1982 |
| JP | 49018875 | A | 2/1974 |
| WO | WO-00/24710 | A | 5/2000 |
| WO | WO-00/24710 | A1 | 5/2000 |
| WO | WO-01/79189 | A2 | 10/2001 |

OTHER PUBLICATIONS

Crowell et al (1992): STN International HCAPLUS database, (Columbus, Ohio), Accession No. 1992:151349.*
Han, Wei (2001): STN International HCAPLUS database, (Columbus, Ohio), Accession No. 2001:416971.*
Database Crossfire Beilstein [Online] Beilstein Institut zur Förderung der Chemischen Wissenschaften, Frankfurt am Main DE; XP002254775, Acta Chem Scand, vol. 15, 1961, p. 1081.
Database Crossfire Beilstein [Online] Beilstein Institut zur Förderung der Chemischen Wissenschaften, Frankfurt am Main DE; XP002254783, Bull Chem Soc Jpn, vol. 64, No. 4, 1991, pp. 1431-1433.
Database Crossfire Beilstein [Online] Beilstein Institut zur Förderung der Chemischen Wissenschaften, Frankfurt am Main DE XP002254784, retrieved from Xfire, Database accerrion No. 8977246, Bioorg Med Chem, vol. 9, No. 11, 2001, pp. 2955-2968.
Data base Crossfire Beilstein [Online] Beilstein Institut zur Förderung der Chemischen Wissenschaften, Frankfurt am Main, DE; XP002254786, Acta Chem Scand, vol. 14, 1960, pp. 1151-1160.
Database Crossfire Beilstein [Online], Beilstein Institut zur Förderung der Chemischen Wissenschaften, Frankfurt am Main, DE; XP002254787 retrieved from Xfire, J Chem Soc., 1960, pp. 3063-3069.
Patrignani, P. et al., "Biochemical and Pharmacological Characterization of the Cyclooxygenase Activity of Human Blood Prostaglandin Endoperoxide Synthases," J.Pharm.Exp.Therapeutics, vol. 271, No. 3, pp. 1705-1712 (1994).
Van Damme, J. et al., "Identification by sequence analysis of chemotactic factors for monocytes produced by normal and transformed cells stimulated with virus, double-stranded RNA or cytokine," Eur.J.Immunol., vol. 19, pp. 2367-2373 (1989).
Francotte, E. R., "Enantioselective chromatography as a powerful alternative for the prepareation of drug enantiomers," J. Chromatogr., vol. 906, pp. 379-397 (2001).

(Continued)

*Primary Examiner*—Golam M Shameem
(74) *Attorney, Agent, or Firm*—Birch, Stewart, Kolasch & Birch, LLP

(57) ABSTRACT

Selected sulfonic acids, their derivatives and pharmaceutical compositions containing such compounds are useful in inhibiting the chemotactic activation of neutrophils (PMN leukocytes) induced by the interaction of Interleukin-8 (IL-8) with CXCR1 and CXCR2 membrane receptors. The compounds are used for the prevention and treatment of pathologies deriving from said activation. Notably, the selected sulfonic acids and their derivativas are devoid of cyclo-oxygenase inhibition activity and are particularly useful in the treatment of neutrofil-dependent pathologies such as psoriasis, ulcerative colitis, melanoma, chronic obstructive pulmonary disease (COPD), bullous pemphigoid, rheumatoid arthritis, idiopathic fibrosis, glomerulonephritis and in the prevention and treatment of damages caused by ischemia and reperfusion.

12 Claims, No Drawings

OTHER PUBLICATIONS http://en.wikipedia.org/wiki/Enantiomeric.
http://en.wikipedia.org/wiki/Chiral_resolution.
http://en.wikipedia.org/wiki/Racemic.
Kawathekar, N., et al., "Synthesis, Biological Evaluation and Qsar Analysis of some new Derivatives of Ketoprofen and Flurbiprofen," India J. Pharm. Sci., vol. 60, No. 6, pp. 346-352 (1998).
Rajasekaran, A., et al., "Systhesis and Evaluation of Antiinflammatory Activity of Ibuprofen Analogs," Indian J. Pharm. Sci., vol. 61, No. 3, pp. 158-161 (1999).
Kwiecien, H., et al., "Synthesis of Amides of Phenylacetic Acids," Polish J. Chem., vol. 65, pp. 2057-2060 (1991).
Niewiadomski, K., et al., "Synthesis of 2-Piperidinepropyl Amides of Expected Antiinflammatory Action," Polish J. Chem., vol. 52, pp. 1805-1807 (1978).
Tsunematsu, H., et al., "Synthesis and the Stereoselective Enzymatic Hydrolysis of Flurbiprofen-Basic Amino Acid Ethyl Esters," J. Drug Tarteting, vol. 2, pp. 517-525 (1995).
Mita, K., et al., "p-Substituted benzylsulfonate salts," retrieved from STN Database accession No. 87:201093 CA XP002254774 & JP 52077030A Jun. 22, 1977, Database CA [Online] Chemical Abstracts Service, Columbus, Ohio, US—ABS.
Bielstein Institut zur Forderung der Chemischen Wissenschaften, Frankfurt am Main, DE; retrieved from XFIRE Database accession No. brn 2110387 XP002254775 & ACTA Chem Scan, 1961—ABS.
Bielstein Institut zur Forderung der Chemischen Wissenschaften, Frankfurt am Main, DE; retrieved from XFIRE Database accession No. 2118685 XP002254776 & Chem Ber, 1898—ABS.
Bielstein Institut zur Forderung der Chemischen Wissenschaften, Frankfurt am Main, DE; retrieved from XFIRE Database accession No. 2208420 XP002254777 & J. Amer. Chem Soc., 1949—ABS.
Bielstein Institut zur Forderung der Chemischen Wissenschaften, Frankfurt am Main, DE; retrieved from XFIRE Database accession No. 2852262 XP002254778 & Bull Acad. Sci. USSR Div. Chem Sci, 1973—ABS.
Bielstein Institut zur Forderung der Chemischen Wissenschaften, Frankfurt am Main, DE; retrieved from XFIRE Database accession No. 2360310 XP002254779 & J Amer Chem Soc, 1946—ABS.
Bielstein Institut zur Forderung der Chemischen Wissenschaften, Frankfurt am Main, DE; retrieved from XFIRE Database accession No. 4649760 XP002254780 & J Amer Chem Soc, 1961—ABS.
Bielstein Institut zur Forderung der Chemischen Wissenschaften, Frankfurt am Main, DE; retrieved from XFIRE Database accession No. 4649760 XP002254781 & Tetrahedron Lett, 1987—ABS.
Bielstein Institut zur Forderung der Chemischen Wissenschaften, Frankfurt am Main, DE; retrieved from XFIRE Database accession No. 210679 XP002254782 & Yakugaku Zasshi, 1958—ABS.
Bielstein Institut zur Forderung der Chemischen Wissenschaften, Frankfurt am Main, DE; retrieved from XFIRE Database accession No. 4742262 XP002254783 & Bull Chem Soc Jpn, 1991—ABS.
Bielstein Institut zur Forderung der Chemischen Wissenschaften, Frankfurt am Main, DE; retrieved from XFIRE Database accession No. 8977246 XP002254784 & Bioorg Med Chem, 2001—ABS.
Bielstein Institut zur Forderung der Chemischen Wissenschaften, Frankfurt am Main, DE; retrieved from XFIRE Database accession No. 2107267 XP002254785 & DE 24 28 223 A, Jan. 2, 1975—ABS.
Bielstein Institut zur Forderung der Chemischen Wissenschaften, Frankfurt am Main, DE; retrieved from XFIRE Database accession No. 2649523 XP002254786 & ACTA Chem Scan, 1960—ABS.
Bielstein Institut zur Forderung der Chemischen Wissenschaften, Frankfurt am Main, DE; retrieved from XFIRE Database accession No. 2652292 XP002254787 & J Chem Soc, 1960—ABS.
Shanbhag, V.R., et al., "Ester and Amide Prodrugs of Ibuprofen and Naproxen: Synthesis, Anti-inflammatory Activity, and Gastrointestinal Toxicity," J. Pharma. Sci., vol. 81, No. 2, pp. 149-154 (1992).
Office Action dated Mar. 6, 2006 for U.S. Appl. No. 10/469,094.
Office Action dated May 9, 2006 for U.S. Appl. No. 10/469,094.
Office Action dated Sep. 28, 2006 for U.S. Appl. No. 10/469,094.
Office Action dated Apr. 17, 2007 for U.S. Appl. No. 10/469,094.
Office Action dated Dec. 11, 2007 for U.S. Appl. No. 10/469,094.
Office Action dated Aug. 29, 2008 for U.S. Appl. No. 10/469,094.
Office Action dated Feb. 20, 2009 for U.S. Appl. No. 10/469,094.
Office Action dated Aug. 4, 2009 for U.S. Appl. No. 10/469,094.
Office Action dated Oct. 6, 2004 for U.S. Appl. No. 10/250,465 (Patent 7,560,487).
Office Action dated Apr. 12, 2005 for U.S. Appl. No. 10/250,465 (Patent 7,560,487).
Office Action dated Nov. 30, 2005 for U.S. Appl. No. 10/250,465 (Patent 7,560,487).
Office Action dated Jun. 15, 2006 for U.S. Appl. No. 10/250,465 (Patent 7,560,487).
Office Action dated Dec. 15, 2006 for U.S. Appl. No. 10/250,465 (Patent 7,560,487).
Office Action dated Feb. 7, 2008 for U.S. Appl. No. 10/250,465 (Patent 7,560,487).
Office Action dated Sep. 29, 2008 for U.S. Appl. No. 10/250,465 (Patent 7,560,487).
Notice of Allowance dated Mar. 11, 2009 for U.S. Appl. No. 10/250,465 (Patent 7,560,487).
Ducheyne, P., et al., "Biomaterials and Biomechanics 1983," Advances in Biomaterials, vol. 5, TOC, 6 pgs.
Niewiadomski, K., et al., "Synthesis of 2-(4-Isobutylpiperidine)-Propyl Amides of Expected Antiinflammator Action," Polish J. Chem., No. 55, pp. 941-945 (1981).

* cited by examiner

SULFONIC ACIDS, THEIR DERIVATIVES AND PHARMACEUTICAL COMPOSITIONS CONTAINING THEM

BRIEF DESCRIPTION OF THE INVENTION

The present invention relates to sulfonic acids and derivatives thereof and to pharmaceutical compositions containing them, which are used in the prevention and treatment of tissue damage due to the exacerbated recruitment of polymorphonucleated neutrophils (PMN leukocytes) at inflammation sites.

STATE OF THE ART

Particular blood cells (macrophages, granulocytes, neutrophils, polymorphonucleated) respond to a chemical stimulus (when stimulated by substances called chemolines) by migrating along the concentration gradient of the stimulating agent, through a process called chemotaxis. The main known stimulating agents or chemokines are represented by the breakdown products of complement C5a, some N-formyl peptides generated from lysis of the bacterial surface or peptides of synthetic origin, such as formyl-methionyl-leucyl-phenylalanine (f-MLP) and mainly by a variety of cytolines, including Interleukin-8 (IL-8, also referred to as CXCL8). Interleukin-8 is an endogenous chemotactic factor produced by most nucleated cells such as fibroblasts and macrophages.

In some pathological conditions, marked by exacerbated recruitment of neutrophils, a more severe tissue damage at the site is associated with the infiltration of neutrophilic cells. Recently, the role of neutrophilic activation in the determination of damage associated with post ischemia reperfusion and pulmonary hyperoxia was widely demonstrated.

The biological activity of IL-8 is mediated by the interaction of the interleukin with CXCR1 and CXCR2 membrane receptors which belong to the family of seven transmembrane receptors, expressed on the surface of human neutrophils and of certain types of T-cells (L. Xu et al., J. Leukocyte Biol., 57, 335, 1995). Selective ligands are known which can distinguish between CXCR1 and CXCR2: GRO-α is an example of a CXCR2 selective chemotactic factor.

Although CXCR1 activation is known to play a crucial role in IL-8-mediated chemotaxis, it has been recently supposed that CXCR2 activation could play a pathophysiological role in cronic inflammatory diseases such as psoriasis. In fact, the pathophysiological role of IL-8 in psoriasis is also supported by the effects of IL-8 on keratinocyte functions.

Indeed, IL-8 has been shown to be a potent stimulator of epidermal cell proliferation as well as angiogenesis, both important aspects of psoriatic pathogenesis (A. Tuschil et al. J Invest Dermatol, 99, 294, 1992; Koch A E et al, Science, 258, 1798, 1992).

In addition, there is accumulating evidence that the pathophysiological role of IL-8 in melanoma progression and metastasis could be mediated by CXCR2 activation (L. R. Bryan et al., Am J Surg, 174, 507, 1997).

The potential pathogenic role of IL-8 in pulmonary diseases (lung injury, acute respiratory distress syndrome, asthma, chronic lung inflammation, and cystic fibrosis) and, specifically, in the pathogenesis of COPD (chronic obstructive pulmonary disease) through the CXCR2 receptor pathway has been widely described (D. WP Hay and H. M. Sarau., Current Opinion in Pharmacology 2001, 1:242-247).

Studies on the contribution of single (S) and (R) enantiomers of ketoprofen to the anti-inflammatory activity of the racemate and on their role in the modulation of the chemokine have demonstrated (P. Ghezzi et al., J. Exp. Pharm. Ther., 287, 969, 1998) that the two enantiomers and their salts with chiral and non-chiral organic bases can inhibit in a dose-dependent way the chemotaxis and increase in intracellular concentration of $Ca^{2+}$ ions induced by IL-8 on human PMN leukocytes (Patent Application U.S. Pat. No. 6,069,172). It has been subsequently demonstrated (C. Bizzarri et al., Biochem. Pharmacol. 61, 1429, 2001) that Ketoprofen shares the property to inhibit the IL-8 biological activity with other molecules belonging to the class of non-steroidal anti-inflammatory NSAIDs) such as flurbiprofen, ibuprofen and indomethacin. The cyclo-oxygenase enzyme (COX) inhibition activity typical of NSAIDs limits the therapeutical application of these compounds in the context of the treatment of neutrophil-dependent pathological states and inflammatory conditions such as psoriasis, idiopathic pulmonary fibrosis, acute respiratory failure, damages from reperfusion and glomerulonephritis. The inhibition of prostaglandin synthesis deriving from the action on cyclo-oxygenase enzymes involves the increase of the cytokine production which, like TNF-α, play a role in amplifying the undesired pro-inflammatory effects of neutrophils.

Novel classes of potent and selective inhibitors of IL-8 biological activities suitable for "in vivo" administration have been discovered. R-2-arylpropionic acid amides and N-acyl-sulfonamides have been described as effective inhibitors of IL-8 induced neutrophils chemotaxis and degranulation (WO 01/58852; WO 00/24710). Furthermore, novel R and S-2-phenylpropionic acids have been recently described as potent IL-8 inhibitors completely lacking the undesired COX inhibitory effect (PCT/EP02/12939).

DETAILED DESCRIPTION OF THE INVENTION

We have now found that a class of sulfonic acids and derivatives thereof show the ability to effectively inhibit IL-8 induced neutrophils chemotaxis and degranulation.

The present invention thus provides use of sulfonic acids and derivatives of formula (I):

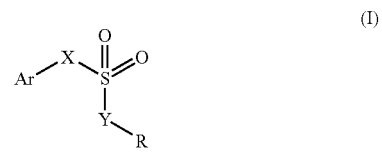

and pharmaceutically acceptable salts thereof, wherein

Ar is a phenyl group, unsubstituted or substituted by one to three substituents, independently selected from halogen, $C_1$-$C_4$-alkyl, $C_1$-$C_4$-alkoxy, hydroxy, $C_1$-$C_4$-acyloxy, phenoxy, cyano, nitro, amino, $C_1$-$C_4$-acylamino, halogen-$C_1$-$C_3$-alkyl, halogen $C_1$-$C_3$-alkoxy, benzoyl, or Ar is a substituted or unsubstituted 5-6 membered heteroaryl ring;

X represents either a —$CH_2$— or a —$CH(CH_3)$— group or an ethylenic group of formula (II) in the E configuration, wherein R' is H or $CH_3$;

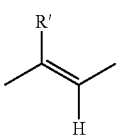

(II)

Y is selected from O (oxygen) and NH; and
when Y is O (oxygen), R is H (hydrogen);
when Y is NH, R is selected from
H, $C_1$-$C_5$-alkyl, $C_1$-$C_5$-cycloalkyl, $C_1$-$C_5$-alkenyl, $C_1$-$C_5$-acyl;
a residue of formula —$CH_2$—$CH_2$—Z—($CH_2$—$CH_2$O)nR" wherein R" is H or $C_1$-$C_5$-alkyl, n is an integer from 0 to 2 and Z is oxygen or sulfur;
a residue of formula —(CH2)n-NRaRb wherein n is an integer from 0 to 5 and each Ra and Rb, which may be the same or different, are $C_1$-$C_6$-alkyl, $C_1$-$C_6$-alkenyl or, alternatively, Ra and Rb, together with the nitrogen atom to which they are bound, form a heterocycle from 3 to 7 members of formula (III)

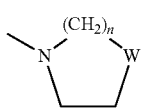

(III)

wherein W represents a single bond, CH2, O, S, N—Rc, Rc being H, $C_1$-$C_6$-alkyl or $C_1$-$C_6$-alkylphenyl, in the preparation of a medicament for the inhibition of IL-8 induced human PMNs chemotaxis.

The term "substituted" in the above definition means substituted with a group selected from $C_1$-$C_5$-alkyl, halogen, hydroxy, $C_1$-$C_5$-alkoxy, amino, $C_1$-$C_5$-alkylamino, nitro, or a cyano group.

Ar is a substituted phenyl group selected from 3'-benzoylphenyl, 3'-(4-chloro-benzoyl)-phenyl, 3'-(4-methyl-benzoyl)-phenyl, 3'-acetyl-phenyl, 3'-propionyl-phenyl, 3'-isobutanoyl-phenyl, 4'-trifluoromethanesulfonyloxy-phenyl, 4'-benzenesulfonyloxy-phenyl, 4'-trifluoromethanesulfonylamino-phenyl, 4'-benzenesulfonylamino-phenyl, 4'-benzenesulfonylmethyl-phenyl, 4'-acetoxyphenyl, 4'-propionyloxy-phenyl, 4'-benzoyloxy-phenyl, 4'acetylaminophenyl, 4'propionylamino-phenyl, 4'-benzoylamino-phenyl, or a heteroaromatic ring selected from pyridine, pyrrole, thiophene, furane, indole.

When Y is NH, preferred R groups are
H, $C_1$-$C_5$ alkyl, $C_1$-$C_5$ acyl;
a residue of formula —$CH_2$—$CH_2$—O—($CH_2$—$CH_2$O)R" wherein R" is H or $C_1$-$C_5$-alkyl;
a residue of formula —(CH2)n-NRaRb wherein n is an integer from 2 to three, more preferably 3 and the group NRaRb is N,N-dimethylamine, N,N-diethylamine, 1-piperidyl, 4-morpholyl, 1-pyrrolidyl, 1-piperazinyl, 1-(4-methyl)piperazinyl;

The present invention further provides novel sulfonic acids and derivative compounds of formula (1), as defined above, selected from:
1-(4-isobutylphenyl) ethanesulfonic acid
1-(4-isobutylphenyl) ethanesulfonic acid
1-[4-(1-oxo-2-isoindolinyl)phenyl]ethanesulfonic acid
1-[4-(1-oxo-2-isoindolinyl)phenyl]ethanesulfonic acid
2-(4-phenylsulfonyloxy)ethanesulfonic acid
2-(4-phenylsulfonyloxy)ethanesulfonic acid
(1-methyl-5-acetylpyrrolyl)-1-methanesulfonic acid
2-(3-benzoylphenyl)ethanesulfonic acid
2-(3-isopropylphenyl)ethanesulfonic acid
E-2-(4-isobutylphenyl)ethenesulfonic acid
E-2-(3-benzoylphenyl)ethenesulfonic acid
E-2-(4-methanesulfonylamainophenyl)ethenesulfonic acid
E-2-(4-trifluoromethanesulfonyloxyphenyl)ethenesulfonic acid
E-2-(4-isobutylphenyl)ethenesulfonamide
E-2-(3-benzoylphenyl)ethenesulfonamide
E-2-[4-(trifluoromethanesulfonyloxy)phenyl]ethenesulfonamide
E-2-[4-(methanesulfonylamino)phenyl]ethenesulfonamide
E-2-(4-isobutylphenyl)ethene-N-(N,N-dimethylaminopropyl)sulfonamide
E-2-(3-benzoylphenyl)ethene-N-(N,N-dimethylaminopropyl)sulfonamide
E-2-[4-(trifluoromethanesulfonyloxy)phenyl]ethene-N-(N,N-dimethylaminopropyl) sulfonamide
E-2-[4-(methanesulfonylamino)phenyl]ethene-N-(N,N-dimethylaminopropyl)sulfonamide
E-2-(4-isobutylphenyl)ethene-N-methyl sulfonamide
E-2-(3-benzoylphenyl)ethene-N-methyl sulfonamide
E-2-[4-(trifluoromethanesulfonyloxy)phenyl]ethene-N-methyl sulfonamide
E-2-[4-(methanesulfonylamino)phenyl]ethene-N-methyl sulfonamide
E-2-(4-isobutylphenyl)ethene-N-(2"-methoxyethyl)sulfonamide
E-2-(3-benzoylphenyl)ethene-N-(2"-methoxyethyl)sulfonamide
E-2-[4-(trifluoromethanesulfonyloxy)phenyl]ethene-N-(2"-methoxyethyl)sulfonamide
E-2-[4-(methanesulfonylamino)phenyl]ethene-N-(2"-methoxyethyl)sulfonamide
(1-methyl-5-isobutirrylpyrrolyl)-1-methanesulfonamide
(1-methyl-5-acetylpyrrolyl)-1-methanesulfonamide
1-(4-isobutylphenyl)ethanesulfonamide
1-(4isobutylphenyl)ethanesulfonamide
1-(3-isopropylphenyl)ethanesulfonamide
1-(4isobutylphenyl)ethane-N-(N,N-dimethylaminopropyl) sulfonamide
1-(3-benzoylphenyl)ethane-N-(N,N-dimethylaminopropyl) sulfonamide
1-[4-(trifluoromethanesulfonyloxy)phenyl]ethane-N-(N,N-dimethylaminopropyl) sulfonamide
1-[4-(methanesulfonylamino)phenyl]ethane-N-(N,N-dimethylaminopropyl)sulfonamide
1-(4-isobutylphenyl)ethane-N-(2-methoxyethyl)sulfonamide
1-(3-benzoylphenyl)ethane-N-(2-methoxyethyl)sulfonamide
1-[4-(trifluoromethanesulfonyloxy)phenyl]ethane-N-(2-methoxyethyl)sulfonamide
1-[4(methanesulfonylamino)phenyl]ethane-N-2-methoxyethyl)sulfonamide
1-(4-isobutylphenyl)ethane-N-methyl sulfonamide
1-(3-benzoylphenyl)ethane-N-methyl sulfonamide
1-[4-(trifluoromethanesulfonyloxy)phenyl]ethane-N-methyl sulfonamide
1-[4-(methanesulfonylamino)phenyl]ethane-N-methyl sulfonamide
1-[4-isobutylphenyl]ethane-N-acetyl sulfonamide
E-2-(3-benzoylphenyl)-2-methyl-ethenesulfonamide
E-2-(3-isopropylphenyl)-2-methyl-ethenesulfonamide E-2-(4-isobutylphenyl)-2-methyl-ethanesulfonamide and pharmaceutically acceptable salts thereof.

Preferably the salt is sodium salt

The ethanesulfonamide described above are chiral compounds and the invention provides both the racemic and the single (+) and (−) enantiomers.

The compounds of the invention of formula (I), when bearing acidic or basic groups, are generally isolated in the form of their addition salts with both organic and inorganic pharmaceutically acceptable acids or bases.

Examples of such acids are selected from hydrochloric acid, sulfuric acid, phosphoric acid, metansolfonic acid, fumaric acid, citric acid.

Examples of such bases are selected from sodium hydroxide, potassium hydroxide, calcium hydroxide, (D,L)-Lysine, L-Lysine, tromethamine.

Compounds of formula (I) wherein YR is OH are obtained by reacting corresponding compounds of formula (IV) wherein J is H or COCH$_3$ with a suitable oxidizing agent such as H$_2$O$_2$, HClO and peroxyacids preferably m-chloroperbenzoic acid.

(IV)

Compounds of formula (I) wherein Y is NH and X is —CH$_2$— are obtained by reacting corresponding sulfonylhalides, such as sulfonylchlorides, with one or two equivalents of an amine of formula NH$_2$R in presence of a suitable organic or inorganic base if necessary.

Compounds of formula (I) wherein Y is NH and X is —CH(CH)$_3$— are obtained by reacting corresponding thiols of formula (IV) with a suitable N-bromoimmide such as N-bromoftalimmide and subsequent oxidation of the sulfur atom followed by deprotection of the sulfonamide derivative as specifically detailed in the examples.

Compounds of formula (I) wherein Y is NH and X is a group of formula (II) are obtained by reacting corresponding sulfonylhalides, such as sulfonylchlorides, with the amine of formula NH$_2$R.

The compounds of the present invention are particularly useful as inhibitors of IL-8 induced human PMNs chemotaxis.

It is a further object of the present invention to provide the novel sulfonic acids and derivative compounds, mentioned above, for use as medicanents.

The compounds of formula (I) were evaluated in vitro for their ability to inhibit chemotaxis of polymorphonucleate leukocytes (hereinafter referred to as PMNs) and monocytes induced by the fractions of IL-8 and GRO-α. For this purpose, in order to isolate the PMNs from heparinized human blood, taken from healthy adult volunteers, mononucleates were removed by means of sedimentation on dextran (according to the procedure disclosed by W. J. Ming et al, J. Immunol., 138, 1469, 1987) and red blood cells by a hypotonic solution. The cell vitality was calculated by exclusion with Trypan blue, whilst the ratio of the circulating polymorphonucleates was estimated on the cytocentrifugate after staining with Diff Quick.

Human recombinant IL-8 (Pepro Tech) was used as stimulating agents in the chemotaxis experiments, giving practically identical results: the lyophilized protein was dissolved in a volume of HBSS containing 0.2% bovin serum albumin (BSA) so thus to obtain a stock solution having a concentration of 10$^{-5}$ M to be diluted in HBSS to a concentration of 10$^{-9}$ M, for the chemotaxis assays.

During the chemotaxis assay (according to W. Falket et al., J. Immunol. Methods, 33, 239, 1980) PVP-free filters with a porosity of 5 μm and microchambers suitable for replication were used.

The compounds of formula (I) were evaluated at a concentration ranging between 10$^{-6}$ and 10$^{-10}$ M; for this purpose they were added, at the same concentration, both to the lower pores and the upper pores of the microchamber. Evaluation of the ability of the compounds of the invention of formula I to inhibit IL-8-induced chemotaxis of human monocytes was carried out according to the method disclosed by Van Damme J. et al. (Eur. J. Immunol., 19, 2367, 1989).

Biological results of some representative compounds in the IL-8 induced PMN chemotaxis test are reported in table II (inhibition data, C=10$^{-8}$ M).

Particularly preferred is the use of compounds of formula (I) in which Ar groups are 3'-benzoylphenyl, 3'-(4-chlorobenzoyl)-phenyl, 3'-(4-methyl-benzoyl)-phenyl, 3'-acetylphenyl, 3'-propionyl-phenyl, 3'-isobutanoyl-phenyl, 4'-trifluoromethanesulfonyloxy-phenyl, 4'-benzenesulfonyloxyphenyl, 4'-trifluoromethanesulfonylamino-phenyl, 4'-benzenesulfonylamino-phenyl, 4'-benzenesulfonylmethyl-phenyl, 4'-acetoxyphenyl, 4'-propionyloxy-phenyl, 4'-benzoyloxy-phenyl, 4'acetylamino-phenyl, 4'propionylamino-phenyl, 4'-benzoylamino-phenyl, which show the additional property to effectively inhibit the GROα induced PMN chemotaxis; this activity allows the therapeutical use of these compounds in IL-8 related pathologies where the CXCR2 pathway is involved specifically or in conjunction with the CXCR1 signaling.

The dual inhibitors of the IL-8 and GRO-α induced biological activities are strongly preferred in view of the therapeutical applications of interest, but the described compounds selectively acting on CXCR1 IL-8 receptor or CXCR2 GRO-α/IL-8 receptor can find useful therapeutical applications in the management of specific pathologies as below described.

The compounds of formula (I), evaluated ex vivo in the blood in toto according to the procedure disclosed by Patrignani et al., in J. Pharmacol. Exper. Ther., 271, 1705, 1994, were found to be totally ineffective as inhibitors of cyclooxygenase (COX) enzymes.

In most cases, the compounds of formula (I) do not interfere with the production of PGE$_2$ induced in murine macrophages by lipopolysaccharides stimulation (LPS, 1 μg/mL) at a concentration ranging between 10$^{-5}$ and 10$^{-7}$ M. Inhibition of the production of PGE$_2$ which may be recorded, is mostly at the limit of statistical significance, and more often is below 15-20% of the basal value. The reduced effectiveness in the inhibition of the CO constitutes an advantage for the therapeutical application of compounds of the invention in as much as the inhibition of prostaglandin synthesis constitutes a stimulus for the macrophage cells to amplify synthesis of TNF-α (induced by LPS or hydrogen peroxide) that is an important mediator of the neutrophilic activation and stimulus for the production of the cytokine Interleukin-8.

In view of the experimental evidence discussed above and of the role performed by Interleukin-8 (IL-8) and congenetics thereof in the processes that involve the activation and the infiltration of neutrophils, the compounds of the invention are particularly useful in the treatment of a disease such as psoriasis (R. J. Nicholoff et al., Am. J. Pathol., 138, 129, 1991). Further diseases which can be treated with the compounds of the present invention are intestinal chronic inflammatory pathologies such as ulcerative colitis (Y. R. Mahida et al., Clin. Sci., 82, 273, 1992) and melanoma, chronic obstructive pulmonary disease (COPD), bullous pemphigo, rheumatoid arthritis (M. Selz et al., J. Clin. Invest., 87, 463, 1981), idiopathic fibrosis (E. J. Miller, previously cited, and P. C. Carré et al., J. Clin. Invest., 88, 1882, 1991), glomerulonephritis (T. Wada et al., J. Exp. Med., 180, 1135, 1994) and in the prevention and treatment of damages caused by ischemia and reperfusion.

Inhibitors of CXCR1 and CXCR2 activation find useful applications, as above detailed, particularly in treatment of chronic inflammatory pathologies (e.g. psoriasis) in which the activation of both IL-8 receptors is supposed to play a crucial pathophysiological role in the development of the disease.

In fact, activation of CXCR1 is known to be essential in IL-8-mediated PMN chemotaxis (Hammond M et al, J Immunol, 155, 1428, 1995). On the other hand, activation of CXCR2 activation is supposed to be essential in IL-8-mediated epidermal cell proliferation and angiogenesis of psoriatic patients (Kulke R et al., J Invest Dermatol, 110, 90, 1998).

In addition, CXCR2 selective antagonists find particularly useful therapeutic applications in the management of important pulmonary diseases like chronic obstructive pulmonary disease COPD (D. WP Hay and H. M. Sarau., Current Opinion in Pharmacology 2001, 1:242-247).

It is therefore a further object of the present invention to provide the use of compounds of formula (I) in the preparation of a medicament for the treatment of psoriasis, ulcerative colitis, melanoma, chronic obstructive pulmonary disease (COPD), bullous pemphigo, rheumatoid arthritis, idiopathic fibrosis, glomerulonephritis and in the prevention and treatment of damages caused by ischemia and reperfusion, as well as the use of such compounds. Pharmaceutical compositions comprising a compound of the invention and a suitable carrier thereof, are also within the scope of the present invention.

The compounds of the invention, together with a conventionally employed adjuvant, carrier, diluent or excipient may, in fact, be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the acids of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermaldermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like.Liquid forms, including the injectable compositions described herebelow, are always stored in the absence of light, so as to avoid any catalytic effect of light, such as hydroperoxide or peroxide formation. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the acid derivative of formula I in such compositions is typically a minor component, frequently ranging between 0.05 to 10% by weight with the remainder being the injectable carrier and the like. The mean daily dosage will depend upon various factors, such as the seriousness of the disease and the conditions of the patient (age, sex and weight). The dose will generally vary from 1 mg or a few mg up to 1500 mg of the compounds of formula (I) per day, optionally divided into multiple administrations. Higher dosages may be administered also thanks to the low toxicity of the compounds of the invention over long periods of time.

The above described components for orally administered or injectable compositions are merely representative. Further materials as well as processing techniques and the like are set out in Part 8 of "Remington's Pharmaceutical Sciences Handbook", $18^{th}$ Edition, 1990, Mack Publishing Company, Easton, Pa., which is incorporated herein by reference.

The compounds of the invention can also be administered in sustained release forms or from sustained release drug delivery systems. A description of representative sustained release materials can also be found in the incorporated materials in the Remington's Handbook as above.

The present invention shall be illustrated by means of the following examples which are not construed to be viewed as limiting the scope of the invention.

EXAMPLE 1

General Procedure for the Synthesis of Arylmethanesulfonic Acids, 1-arylethanesulfonic Acids of Formula R—Ar—C(CH$_3$)H—SO$_3$H and Related Enantiomers To a cooled (T=0-4° C.) solution of the substituted benzene (17 mmol) and acetyl chloride (18 mmol) in dry CH$_2$Cl$_2$ (25 mL), AlCl$_3$ (18 mmol) is added portionwise under vigorous stirring. The ice bath is then removed and the solution is refluxed until complete disappearance of the starting material is evident (2-3 hours). After cooling at room temperature, the mixture is poured into cooled 2N HCl and left stirring for 30'. The acid solution is then transferred into a separator funnel and extracted with CH$_2$Cl$_2$ (3×20 mL). The collected organic extracts are washed with a NaCl saturated solution (2×25 mL), dried over Na$_2$SO$_4$ and evaporated under vacuum to give the pure arylacetophenone (14.45-16.15 mmol) in high yield (85-95%).

To a stirred solution of arylacetophenone (11.5 mmol) in methyl alcohol (40 mL) sodium borohydride (17.2 mmol) is added portionwise. The mixture is refluxed until the starting material is completely disappeared (3 hours). After cooling at room temperature, 1M HCl is added to the mixture and the alcohol is distilled off. The aqueous phase is extracted with ethyl acetate (3×15 mL) and the collected organic extracts are washed with a NaCl saturated solution (2×15 mL), dried over Na$_2$SO$_4$ and evaporated under vacuum to give the pure 1-arylethyl alcohol (yield around 75%).

To a stirred solution of 1-arylethyl alcohol (4.5 mmol) in dry CHCl$_3$ (10 mL) thiolacetic acid (5.39 mmol) and zinc iodide (2.24 mmol) are added. The reaction mixture is refluxed for 3 hours; after cooling at room temperature, the mixture is diluted with water (15 mL) and transferred into a separator funnel. The two phases are shaken and separated. The organic phase is washed with a NaHCO$_3$ saturated solution (3×20 mL), then with a NaCl saturated solution, dried over Na$_2$SO$_4$ and evaporated under vacuum to give the pure 1-arylethylthioacetate (yield around 80%).

A solution of 1-arylethylthioacetate (0.91 mmol) in glacial acetic acid (2 mL) is stirred at 60° C. and treated dropwise with 30% H$_2$O$_2$ (4.56 mmol); the resulting solution is stirred at 60° C. for 24 hours, then the acetic acid is removed azeotropically with toluene. The residue is diluted with water (5 mL), neutralised with 1N NaOH, washed with diethyl ether (2×15 mL) and lyophilised to provide the 1-arylethanesulfonic acid sodium salt as racemic mixture as a white solid (yield around 90%).

Optical Resolution

Racemic 1-arylethanesulfonic acid sodium salt is filtered through a column packed with Amberlite IR-120 resin (H+ form) eluted with water to give the product as pasty oil. The two isomers separation is achieved by crystalisation of the corresponding (+) or (−) α-phenylethylammonium salts in ethanolic solution as described for the optical resolution of arylpropionic acids in Akgun H. et al., Arzneim.-Forsch./Drug Res., 46(II), Nr.9, 891-894 (1996). The pure enantiomers are isolated as sodium salts.

According to the above described method, the following compounds have been prepared:

(−)-1-(4-isobutylphenyl)ethanesulfonic acid sodium salt (1)

The compound has been synthesised starting from commercial isobutylbenzene.

[α]D =−35 (c=1; H$_2$O) $^1$H-NMR (DMSO-d$_6$): δ 7.25 (d, 2H, J=7 Hz); 7.05 (d, 2H, J=7 Hz); 3.62 (m, 1H); 2.37 (d, 2H, J=7 Hz); 1.86 (m, 1H); 1.40 (d, 3H, J=7 Hz); 0.91 (d, 6H, J=7 Hz).

(+)-1-(4-isobutylphenyl)ethanesulfonic acid sodium salt (2)

The compound has been synthesised starting from commercial isobutylbenzene.

[α]$_D$=+34.5 (c=1; H$_2$O) $^1$H-NMR (DMSO-d$_6$): δ 7.25 (d, 2H, J=7 Hz); 7.08 (d, 2H, J=7 Hz); 3.62 (m, 1H); 2.37 (d, 2H, J=7 Hz); 1.86 (m, 1H); 1.42 (d, 3H, J=7 Hz); 0.90 (d, 6H, J=7 Hz).

(−)-1-[4-(1-oxo-2-isoindolinyl)phenyl]ethanesulfonic acid sodium salt (3)

The compound has been prepared according to the above described method starting from the intermediate 4-(1-oxo-2-isoindolinyl)acetophenone. This intermediate has been prepared from the commercially available reagents phtalaldehyde and 4-aminoacetophenone on the basis of the method described in ichiro, T. et al., Heterocycles 43: 11, 2343-2346 (1996).

[α]$_D$=−52.4 (c=1; H$_2$O) $^1$H-NMR (DMSO-d$_6$): δ 7.68 (m, 3H); 7.35 (m, 3H); 7.15 (d, 2H, J=7 Hz); 4.68 (s, 2M); 3.65 (q, 1H, J=7 Hz, J2=3 Hz); 1.28 (d, 3H, J=7 Hz).

(+)-1-[4-1-oxo-2-isoindolinyl)phenyl] ethanesulfonic acid sodium salt (4)

The compound has been prepared according to the above described method starting from the intermediate 4-(1-oxo-2-isoindolinyl)acetophenone. This intermediate has been prepared from the commercially available reagents phtalaldehyde and 4-aminoacetophenone on the basis of the method described in Ichiro, T. et al., Heterocycles 43: 11, 2343-2346 (1996).

[α]$_D$=+50 (c=1; H$_2$O) $^1$H-NMR (DMSO-d$_6$): δ 7.708 (m, 3H); 7.35 (m, 3H); 7.18 (d, 2H, J=7 Hz); 4.68 (s, 2H); 3.65 (q, 1H, J=7 Hz, J2=3 Hz); 1.30 (d, 3H, J=7 Hz).

(−)-2-(4-phenylsulfonyloxy)ethanesulfonic acid sodium salt (5)

The compound has been prepared according to the above described method starting from the intermediate 4-benzenesulfonyloxyacetophenone obtained from the commercial 4-hydroxyacetophenone following known experimental procedures.

[α]$_D$=−47.5 (c=1; H$_2$O) $^1$H-NMR (D$_2$O): δ 7.90 (d, 2H, J=7 Hz); 7.70 (t, 1H, J=7 Hz); 7.55 (t, 2H, J=7 Hz); 7.32 (d, 2H, J=7 Hz); 6.95 (d, 2H, J=7 Hz); 3.64 (m, 1H); 1.41 (d, 3H, J=7 Hz).

(+)-2-(4-phenylsulfonyloxy)ethanesulfonic acid sodium salt (6)

The compound has been prepared according to the above described method starting from the intermediate 4-benzenesulfonyloxyacetophenone obtained from the commercial 4-hydroxyacetophenone following known experimental procedures.

[α]$_D$=+49 (c=1; H$_2$O) $^1$H-NMR (D$_2$O): δ 7.93 (d, 2H, J=7 Hz); 7.70 (t, 1H, J=7 Hz); 7.55 (t, 2H, J=7 Hz); 7.32 (d, 2H, J=7 Hz); 6.91 (d, 2H, J=7 Hz); 3.67 (m, 1H); 1.41 (d, 3H, J=7 Hz).

(1-methyl-5-acetylpyrrolyl)1-methanesulfonic acid sodium salt (7)

The synthesis of (7) has been carried out starting from the commercial reagent methyl-1-methyl-2-pyrrole acetate that, by Friedel Cafts acylation with acetyl chloride, has afforded the (1-methyl-5-acetylpyrrolyl)-1-methaneacetate. The ester group then has been hydrolysed. Following the experimental procedure described in WO 02/0704095 the related (1-methyl-5-acetylpyrrolyl)-1-methanesulfonic acid sodium salt has been obtained.

$^1$H-NMR (DMSO-d$_6$): δ 7.5 (s, 1H); 6.18 (s, 1H); 3.60 (s, 3H); 3.51 (s, 2H); 2.10 (s, 3H).

(±)-2-(3-benzoylphenyl) ethanesulfonic acid sodium salt (8)

The synthesis of (8) has been carried out starting from the commercial reagent 3-(1-cyanoethyl)benzoic acid that, by Friedel Crafts acylation in benzene, has afforded the 2-(3'-benzoylphenyl)propionitrile. Following the experimental procedure described in WO 02/0704095 the related 2-(3'-benzoylphenyl)ethanesulfonic acid sodium salt has been obtained.

$^1$H-NMR (D$_2$O): δ 7.80 (d, 2H, J=7 Hz); 7.70 (s, 1H); 7.62 (d, 1H, J=7 Hz); 7.51 (m, 2H); 7.30 (m, 3); 3.62 (m, 1H); 1.40 (d, 3H, J=7 Hz).

(±)-2-(3-isopropylphenyl)ethanesulfonic acid sodium salt (9)

The synthesis of (9) has been carried out starting from the available reagent 3-(1-cyanoethyl)acetophenone that, by Wittig reaction and reduction of the methylene group according well known methods, has afforded the 2-(3-isopropylphenyl) propionitrile. Following the experimental procedure described in WO 02/0704095 the related 2-(3-isopropylphenyl)ethanesulfonic acid sodium salt has been obtained.

$^1$H-NMR (D$_2$O): δ 7.30 (m, 2H); 7.10 (m, 2H); 3.92 (m, 1H); 3.63 (m, 1H); 1.42 (d, 3H, J=7 Hz); 1.25 (d, 6H, J=8 Hz).

EXAMPLE 2

Preparation of E-arylethenesulfonic acids (sodium salts)

The arylethanesulfonic acid is dissolved in thionyl chloride (5 mL) and the solution is left under reflux overnight. After cooling at room temperature, thionyl chloride is evaporated under vacuum and the crude arylethanesulfonyl chloride is diluted with dry THF (5 mL) and cooled at T=0° C. in an ice-water bath; 1N aqueous NaOH (0.64 mmol) is added at T=4° C.; the ice-water bath is removed and the reaction mixture is left still until it reaches room temperature in about one hour, while a white solid precipitates. The organic sodium salt is filtered under vacuum, washed with THF and dried in oven under vacuum at 40° C. to give the pure E-arylethenesulfonic acid sodium salt (0.32-0.51 mmol) (yield 50-80%) as white powder.

According to the above described procedure, the following compounds have been prepared:

E-2-(4-isobutylphenyl)ethenesulfonic acid sodium salt (10)

$^1$H-NMR (D$_2$O): δ 7.60 (d, 1H, J=8 Hz); 7.55-7.32 (m, 4H); 7.05 (d, 1H, J=14 Hz); 2.62 (m, 2H); 1.90 (m, 1H); 0.97 (d, 6H, J=7 Hz).

E-2-(3-benzoylphenyl)ethenesulfonic acid sodium salt (11)

$^1$H-NMR (D$_2$O): δ 7.80 (d, 2H, J=7 Hz); 7.70 (s, 1H); 7.65 (d, 1H, J=8 Hz); 7.62 (d, 1H, J=7 Hz); 7.51 (m, 2H); 7.30 (m, 3H); 7.00 (d, 1H, J=14 Hz).

E-2-(4-methanesulfonylaminophenyl)ethenesulfonic acid sodium salt (12)

$^1$H-NMR (DMSO-d$_6$): δ 7.60 (d, 1H, J=8 Hz); 7.35 (d, 2H, J=8 Hz); 7.20 (d, 2H, J=8 Hz); 7.07 (d, 1H, J=14 Hz); 6.51 (bs, 1H, SO$_2$NH); 3.00 (s, 3H).

E-2-(4-trifluoromethanesulfonyloxyphenyl)ethenesulfonic acid sodium salt (13)

$^1$H-NMR (CDCl$_3$): δ 7.62 (d, 1H, J=8 Hz); 7.50 (d, 2H, J=7 Hz); 7.25 (d, 2H, J=7 Hz); 7.05 (d, 1H, J=14 Hz).

EXAMPLE 3

General Procedure for the Synthesis of E-arylethenesulfonamides

A solution of the arylethanesulfonic acid (0.64 mmol) is dissolved in thionyl chloride (5 mL) and the solution is left under reflux overnight After cooling at room temperature, thionyl chloride is evaporated under vacuum and the crude arylethanesulfonyl chloride is diluted with dry THF (5 mL) and cooled at T=0° C. in an ice-water bath; the selected amine (1.28 mmol) is added dropwise. The ice-water bath is removed and the reaction mixture is left to reach room temperature. After the complete disappearance of the starting reagent the solvents are evaporated under vacuum and CHCl$_3$ (10 mL) and water (10 mL) are added to the residue; the two phases are shaken and separated, the organic phase is washed with water (3×15 mL), dried over Na$_2$SO$_4$ and evaporated under vacuum to give a crude which is purified by flash chromatography. Pure E/Z-aryl ethenesulfonamides (0.32-0.51 mmol) (yield 50-80%) are isolated as colourless oils.

According to the above described method, and using ammonia (0.5 M in 1,4-dioxane) as the amine, the following compounds have been prepared:

E-2-(4-isobutylphenyl)ethenesulfonamide (14)

$^1$H-NMR (CDCl$_3$): δ 7.55 (d, 1H, J=14 Hz); 7.38 (d, 2H, J=7 Hz); 7.18 (d, 2H, J=7 Hz); 6.88 (d, 1H, J=14 Hz); 4.75 (bs, 2H, SO$_2$NH$_2$); 2.55 (d, 2H, J=7 Hz); 1,94 (m, 1H); 1.02 (d, 6H, J=7 Hz).

E-2-(3-benzoylphenyl)ethenesulfonamide (15)

$^1$H-NMR (CDCl$_3$): δ 7.80 (d, 2H, J=7 Hz); 7.72 (s, 1H); 7.62 (d, 1H, J=8 Hz); 7.52 (d, 1H, J=14 Hz); 7.50 (m, 2H); 7.30 (m, 3H); 6.88 (d, 1H, J=14 Hz); 4.75 (bs, 2H, SO$_2$NH$_2$).

E-2-[4-(trifluoromethanesulfonyloxy)phenyl]ethenesulfonamide (16)

$^1$H-NMR (CDCl$_3$): δ 7.60 (d, 1H, J=8 Hz); 7.52 (d, 2H, J=7 Hz); 7.28 (d, 2H, J=7 Hz); 7.10 (d, 1H, J=14 Hz); 4.85 (bs, 2H, SO$_2$NH$_2$).

E-2-[4-(methanesulfonylamino)phenyl]ethenesulfonamide (17)

$^1$H-NMR (CDCl$_3$): δ 7.55 (d, 1H, J=14 Hz); 7.37 (d, 2H, J=8 Hz); 7.22 (d, 2H, J=8 Hz); 6.90 (d, 1H, J=14 Hz); 6.45 (bs, 1H, SO$_2$NH); 4.80 (bs, 2H, SO$_2$NH$_2$); 2.98 (s, 3H).

According to the above described method, and using 3-(dimethylamino)propylamine as the amine, the following compounds have been prepared:

E-2-(4-isobutylphenyl)ethene-(N,N-dimethylaminopropyl)sulfonamide (18)

$^1$H-NMR (CDCl$_3$): δ 7.45 (m, 3H); 7.20 (d, 2H, J=7 Hz); 6.70 (d, 1H, J=14 Hz); 6.40 (bs, 1H, SO$_2$NH); 3.18 (m, 2H); 2.55 (m, 4H); 2.30 (s, 6H); 1.92 (m, 1H); 1.75 (m, 2H); 0.97 (d, 6H, J=7 Hz).

E-2-(3-benzoylphenyl)etheneN-(N,N-dimethylaminopropyl)sulfonamide (19)

$^1$H-NMR (CDCl$_3$): δ 7.82 (d, 2H, J=7 Hz); 7.74 (s, 1H); 7.60 (d, 1H, J=8 Hz); 7.50 (d, 1H, J=14 Hz); 7.45 (m, 2H); 7.26 (m, 3H); 6.70 (d, 1H, J=14 Hz); 6.45 (bs, 1H, SO$_2$NR); 3.15 (m, 2H); 2.50 (m, 4H); 2.35 (s, 6H).

E-2-[4-(trifluoromethanesulfonyloxy)phenyl]ethene-(N,N-dimethylaminopropyl)sulfonamide (20)

$^1$H-NMR (CDCl$_3$): δ 7.62 (d, 1H, J=14 Hz); 7.48 (d, 2H, J=7 Hz); 7.25 (d, 2H, J=7 Hz); 7.00 (d, 1H, J=14 Hz); 6.50 (bs, 1, SO$_2$NH); 3.17 (m., 2H); 2.48 (m, 4H); 2.35 (s, 6H).

E-2-[4-(methanesulfonylamino)phenyl]ethene-(N,N-dimethylaminopropyl)sulfonamide (21)
$^1$H-NMR (CDCl$_3$): δ 7.57 (d, 1H, J=14 Hz); 7.37 (d, 2H, J=8 Hz); 7.22 (d, 2H, J=8 Hz); 6.75 (d, 1H, J=14 Hz); 6.50 (bs, 2H, SO$_2$NH); 3.15 (m, 2H); 2.98 (s, 3H); 2.50 (m, 4H); 2.40 (s, 6H).

According to the above described method, and using methylamine (2M in THF) as the amine the following compounds have been prepared:

E-2-(4-isobutylphenyl)ethene-N-methyl sulfonamide (22)
$^1$H-NMR (CDCl$_3$): δ 7.55 (d, 1H, J=14 Hz); 7.38 (d, 2H, J=7 Hz); 7.18 (d, 2H, J=7 Hz); 6.88 (d, 1H, J=14 Hz); 4.80 (bs, 1H, SO$_2$NH); 2.75 (d, 3H, J=4 Hz); 2.55 (d, 2H, J=7 Hz); 1.95 (m, 1H); 1.04 (d, 6H, J=7 Hz).

E-2-(3-benzoylphenyl)ethene-N-methyl sulfonamide (23)
$^1$H-NMR (CDCl$_3$): δ 7.81 (d, 2H, J=7 Hz); 7.70 (s, 1H); 7.62 (d, 1H, J=8 Hz); 7.55 (d, 1H, J=14 Hz); 7.45 (m, 2H); 7.30 (m, 3H); 6.90 (d, 1H, J=14 Hz); 4.60 (bs, 1H, SO$_2$NH); 2.70 (d, 3H, J=4 Hz).

E-2-[4-(trifluoromethanesulfonyloxy)phenyl]ethene-N-methyl sulfonamide (24)
$^1$H-NMR (CDCl$_3$): δ 7.60 (d, 1H, J=8 Hz); 7.52 (d, 2H, J=7 Hz); 7.28 (d, 2H, J=7 Hz); 7.10 (d, 1H, J=14 Hz); 4.85 (bs, 1H, SO$_2$NH); 2.70 (d, 3H, J=4 Hz).

E-2-[4-(methanesulfonylamino)phenyl]ethene-N-methyl sulfonamide (25)
$^1$H-NMR (CDCl$_3$): δ 7.56 (d, 1H, J=14 Hz); 7.35 (d, 2H, J=8 Hz); 7.20 (d, 2H, J=8 Hz); 6.92 (d, 1H, J=14 Hz); 6.50 (bs, 1H, SO$_2$NH); 4.70 (bs, 1H, SO$_2$NH); 3.00 (s, 3H), 2.75 (d, 3H, J=4 Hz).

According to the above described method, and using 2-methoxyethylamine as the amine the following compounds have been prepared:

E-2-(4isobutylphenyl)ethene-N-2-methoxyethyl)sulfonamide (26)
$^1$H-NMR (CDCl$_3$): δ 7.57 (d, 1H, J=14 Hz); 7.38 (d, 2H, J=7 Hz.); 7.20 (d, 2H, J=7 Hz); 6.90 (d, 1H, J=14 Hz); 4.80 (bs, 1H, SO$_2$NH); 3.74 (m, 2H); 3.55 (m, 2H); 3.45 (s, 3H); 2.52 (d, 2H, J=7 Hz.); 1.95 (m, 1H); 1.05 (d, 6H, J=7 Hz).

E-2-(3-benzoylphenyl)ethene-N-(2-methoxyethyl)sulfonamide (27)
$^1$H-NMR (CDCl$_3$): δ 7.80 (d, 2H, J=7 Hz); 7.72 (s, 1H); 7.62 (d, 1H, J=8 Hz); 7.55 (d, 1H, J=14 Hz); 7.40 (m, 2H); 7.30 (m, 3H); 6.95 (d, 1H, J=14 Hz); 4.62 (bs, 1H, SO$_2$NH); 3.75 (m, 2H); 3.50 (m, 2H); 3.40 (s, 3H).

E-2-[4-(trifluoromethanesulfonyloxy)phenyl]ethen-N-(2-methoxyethyl)sulfonamide (28)
$^1$H-NMR (CDCl$_3$): δ 7.62 (d, 1H, J=8 Hz); 7.50 (d, 2H, J=7 Hz); 7.30 (d, 2H, J=7 Hz); 7.15 (d, 1H, J=14 Hz); 4.80 (bs, 1H, SO$_2$NH); 3.77 (m, 2H); 3.52 (m, 2H); 3.40 (s, 3H).

E-2-[4-(methanesulfonylamino)phenyl]ethen-N-(2-methoxyethyl)sulfonamide (29)
$^1$H-NMR (CDCl$_3$): δ 7.58 (d, 1H, J=14 Hz); 7.35 (d, 2H, J=8 Hz); 7.25 (d, 2H, J=8 Hz); 6.90 (d, 1H, J=14 Hz); 6.52 (bs, 1H, SO$_2$NH); 4.75 (bs, 1H, SO$_2$NH); 3.70 (m, 2H); 3.50 (m, 2H); 3.40 (s, 3H); 3.05 (s, 3H).

EXAMPLE 4

General Procedure for the Synthesis of arylmethanesulfonamides (1-methyl-5-isobutirrylpyrrolyl)-1-methanesulfonamide (30)

The synthesis of (30) has been carried out starting from the commercial reagent methyl-1-methyl-2-pyrrole acetate that, by Friedel Crafts acylation with isobuturryl chloride, has afforded the (1-methyl-5-isobutirrylpyrrolyl)-1-methaneacetate. The ester group then has been hydrolysed. Following the experimental procedure described in WO 02/0704095, the related (1-methyl-5-isobutirrylpyrrolyl)-1-methanesulfonic acid sodium salt has been obtained.

A solution of (1-methyl-5-isobutirrylpyrrolyl)-1-methanesulfonic acid sodium salt (0.64 mmol) is dissolved in thionyl chloride (5 mL) and the solution is left under reflux overnight. After cooling at room temperature, thionyl chloride is evaporated under vacuum and the crude (1-methyl-5-isobutirrylpyrrolyl)-1-methanesulfonyl chloride is diluted with dry THF (5 mL) and cooled at T=0° C. in an ice-water bath; the solution of ammonia (1.28 mmol) is added dropwise. The ice-water bath is removed and the reaction mixture is left to reach room temperature. After the complete disappearance of the starting reagent the solvents are evaporated under vacuum and CHCl$_3$ (10 mL) and water (10 mL) are added to the residue; the two phases are shaken and separated, the organic one is washed with water (3×15 mL), dried over Na$_2$SO$_4$ and evaporated under vacuum to give a crude which is purified by flash chromatography. Pure (1-methyl-5-isobutirrylpyrrolyl)-1-methanesulfonamide (0.60 mmol) (yield 93%) are isolated as a yellow oil.

$^1$H-NMR (DMSO-d$_6$): δ 7.5 (s, 1H); 6.18 (s, 1H); 4.65 (bs, 2H, SO$_2$NH$_2$); 3.60 (s, 3H); 3.51 (s, 2H); 3.38 (m, 1H); 1.25 (d, 6H, J=8 Hz).

According to the above described method, and using (1-methyl-5-acetylpyrrolyl)-1-methanesulfonic acid sodium salt (7) (prepared according to the above described method of general procedure for the synthesis of arymethanesulfonic acids) the following compound has been prepared:

(1-methyl-5-acetylpyrrolyl)-1-methanesulfonamide (31)
$^1$H-NMR (DMSO-d$_6$): δ 7.5 (s, 1H); 6.18 (s, 1H); 4.40 (bs, 2H, SO$_2$NH$_2$); 3.60 (s, 3H); 3.51 (s, 2H); 2.10 (s, 3H).

Enantioselective Synthesis of (+) and (−) Enantiomers of Compounds 32 and 33

The enantioselective synthesis of (+) and (−) enantiomers of 1-(4-isobutylphenyl)ethanesulfonamide has been performed as described in Davis F. A. et al., J. Org. Chem., 58, 4890-4896, (1993). The procedure involves the diastereoselective C-methylation of N-sulfonylcamphorimine generated from 4-isobutylbenzylsulfonamide (27) and N,N-diisopropyl-(1S)-(+)-10-camphorsulfonamide or N,N-diisopropyl-(1R)-(−)-10-camphorsulfonamide. The diastereoisomers acid hydrolysis allows to obtain the desired compounds, both as transparent oils.

(−)-1-(4-isobutylphenyl)ethanesulfonamide (32)
[α]$_D$=−8.5 (c=1.2; CHCl$_3$) $^1$H-NMR (CDCl$_3$): δ 7.30 (d, 2H, J=7 Hz); 7.18 (d, 2H, J=7 Hz); 4.25 (m, 1H+bs SONH$_2$); 2.45 (d, 2H, J=7 Hz); 1.87 (m, 4H); 0.97 (d, 6H, J=7 Hz).

(+)-1-(4-isobutylphenyl)ethanesulfonamide (33)
[α]$_D$=+15 (c=1; CHCl$_3$) $^1$H-NMR (CDCl$_3$): δ 7.30 (d, 2H, J=7 Hz); 7.18 (d, 2H, J=7 Hz); 4.25 (m, 1H+bs SONH$_2$); 2.45 (d, 2H, J=7 Hz); 1.87 (m, 4H); 0.97 (d, 6H, J=7 Hz).

EXAMPLE 5

Alternative Synthesis of Arylethanesulfonamides

Synthesis of (+)-1-(3-isopronylphenyl)ethanesulfonamide (34)

The title compound has been prepared starting the commercial reagent 3-(1-cyanoethyl)benzoic acid which, following the experimental procedures described in Kindler K. et al., Chem. Ber., 99, 226 (1966) and in Kindler K. et al., Liebigs Ann. Chem., 26, 707 (1967), has afforded the intermediate 3-isopropyl benzoic acid. Reduction to benzylalcohol derivative by LiAlH$_4$ and subsequent treatment of the alcohol with thiolacetic acid has given the intermediate ethylthioacetate. The subsequent hydrolysis to the thiol derivative has been carried out as described in Corey E. J. et al., Tet. Lett., 33, 4099 (1992).

To a suspension of 3-isopropylbenzyl thiol (3.85 g; 23.2 mmol) and potassium ter-butoxide (2.6 g; 23.2 mmol) in CH$_2$Cl$_2$ (15 mL), 18-Crown-6 (0.6 g; 2.3 mmol) is added. After stirring for 15' at T=0°-4° C. N—Br-phtalimide (5.24 g; 23.2 mmol) is added. After the adding the ice-water bath is removed and the solution is left stirring at room temperature for 1 h; then the organic phase is washed with water (3×15 mL), dried over Na2SO4 and evaporated under vacuum to give an oily residue purified by flash chromatography to give 3-isopropylbenzylthiophtalimide (6.05 g; 18.56 mmol) as a pale yellow oil (yield 80%). The following methylation to give the racemic 1-(3-isopropylphenyl)ethyl thiophtalimide has been carried out as described in Davis F. A. et al., J. Org. Chem., 58, 4890-4896, (1993). The final compound 1-(3-isopropylphenyl)ethanesulfonamide (31) has been obtained by oxidation with 3-chloroperbenzoic acid (2 equivalents) and cleavage of the phtalimido moiety by treatment with hydrazine according to methods well known in the art.

$^1$H-NMR (CDCl$_3$): δ 7.28 (m, 2H); 7.05 (m, 2H); 4.40 (bs, 2H, SO$_2$NH$_2$); 3.90 (m, 1H); 3.65 (m, 1H); 1.35 (d, 3H, J=7 Hz); 1.20 (d, 6H, J=8 Hz).

Alkylation of the corresponding 1-arylethanesulfonamides (prepared according to the above described method) by 3-dimethylaminopropyl chloride as alkylating reagent has been carried out in phase transfer conditions as described in Gajda T. et al., Synthesis, 1005 (1981) and Burke P.O. et al., Synthesis, 935 (1985). The following compounds have been prepared:

(±)-1-(4-isobutylphenyl)ethane-N-(N,N-dimethylaminopropyl)sulfonamide (35)

$^1$H-NMR (CDCl$_3$): δ 7.32 (d, 2H, J=7 Hz); 7.18 (d, 2H, J=7 Hz.); 4.26 (m, 1H); 4.10 (bs, 1H, SONH); 3.18 (m, 2H); 2.55 (m, 4H); 2.45 (d, 2H, J=7 Hz); 2.40 (s, 6H); 1.85(m, 4H); 1.00 (d, 6H, J=7 Hz).

(±)-1-(3-benzoylphenyl)ethane-N-(N,N-dimethylaminopropyl)sulfonamide (36)

$^1$H-NMR (CDCl$_3$): δ 7.80 (d, 2H, J=7 Hz); 7.70 (s, 1H); 7.62 (d, 1H, J=7 Hz); 7.51 (m, 2H); 7.30 (m, 3H); 4.35 (bs, 1H, SO$_2$NH); 3.62 (m, 1H); 3.18 (m, 2H); 2.55 (m, 4H); 2.40 (s, 6H); 1.30 (d, 3H, J=7 Hz).

(±)-1-[4-(trifluoromethanesulfonyloxy)phenyl]ethane-N-(N,N-dimethylaminopropyl)sulfonamide (37)

$^1$H-NMR (CDCl$_3$): δ 7.50 (d, 2H, J=7 Hz); 7.25 (d, 2H, J=7 Hz); 4.30 (bs, 1H, SO$_2$NH); 3.85 (m, 1H); 3.20 (m, 2H); 2.60 (m, 4H); 2.45 (s, 6H); 1.25 (d, 3H, J=7 Hz).

(±) 1-[4-(methanesulfonylamino)phenyl]ethane-N-(N,N-dimethylaminopropyl)sulfonamide (38)

$^1$H-NMR (CDCl$_3$): δ 7.37 (d, 2H, J=8 Hz); 7.22 (d, 2H, J=8 Hz); 6.45 (bs, 1H, SO2NH); 4.80 (bs, 1H, SO$_2$NH); 3.82 (m, 1H); 3.25 (m, 2H); 2.98 (s, 3H); 2.65 (m, 4H); 2.45 (s, 6H); 1.05 (d, 3H, J=7 Hz).

Alkylation of the corresponding 1-arylethanesulfonamides (prepared according to the above described method) by 2-bromoethylmethyl ether as alkylating reagent has been carded out in phase transfer conditions as described in Gajda T. et al., Synthesis, 1005 (1981) and Burke P.O. et al., Synthesis, 935 (1985). The following compounds have been prepared:

(±)-1-(4-isobutylphenyl)ethane-N-(2-methoxyethyl)sulfonamide (39)

$^1$H-NMR (CDCl$_3$): δ 7.30 (d, 2H, J=7 Hz); 7.18 (d, 2H, J=7 Hz); 4.25 (m, 1H); 4.80 (bs, 1H, SO$_2$NH); 3.74 (m, 2H); 3.55 (m, 2H); 3.45 (s, 3H); 2.45 (d, 2H, J=7 Hz); 1.87 (m, 1H); 1.65 (d, 3H, J=7 Hz); 0.97 (d, 6H, J=7 Hz).

(±)-1-(3-benzoylphenyl)ethane-N-(2-methoxyethyl)sulfonamide (40)

$^1$H-NMR (CDCl$_3$): δ 7.82 (d, 2H, J=7 Hz); 7.75 (s, 1H); 7.62 (d, 1H, J=7 Hz); 7.55 (m, 2H); 7.30 (m, 3H); 4.25 (bs, 1H, SO$_2$NH); 3.75 (m, 2H); 3.60 (m, 1H); 3.55 (m, 2H); 3.48 (s, 3H); 1.55 (d, 3H, J=7 Hz).

(±)-1-[4-(trifluoromethanesulfonyloxy)phenyl]ethane-N-(2-methoxyethyl)sulfonamide (41)

$^1$H-NMR (CDCl$_3$): δ 7.50 (d, 2H, J=7 Hz); 7.25 (d, 2H, J=7 Hz); 4.30 (bs, 1H, SO$_2$NH); 3.85 (m, 1H); 3.60 (m, 2H); 3.55 (m, 2H); 3.48 (s, 3H); 1.35 (d, 3H, J=7 Hz).

(±)-1-[4-(methanesulfonylamino)phenyl]ethane-N-(2-methoxyethyl)sulfonamide (42)

$^1$H-NMR (CDCl$_3$): δ 7.52 (d, 2H, J=7 Hz); 7.28 (d, 2H, J=7 Hz); 6.45 (bs, 1H, SO$_2$NH); 4.32 (bs, 1H, SO$_2$NH); 3.85 (m, 1H); 3.62 (m, 2M); 3.55 (m, 2H); 3.48 (s, 3H); 3.00 (s, 3H); 1.35 (d, 3H, J=7 Hz).

Monomethylation of the corresponding 1-arylethanesulfonamides (prepared according to the above described method) by diazomethane has been carried out as described in Muller E. et al., Liebigs Ann. Chem., 623, 34 (1959) and Saegusa T. et al., Tet Lett., 6131 (1966). The following compounds have been prepared:

(±)-1-(4-isobutylphenyl)ethane-N-methyl sulfonamide (43)

$^1$H-NMR (CDCl$_3$): δ 7.25 (d, 2H, J=7 Hz); 7.18 (d, 2H, J=7 Hz); 4.80 (bs, 1H, SO$_2$NH); 4.20 (m, 1H); 2.70 (d, 3H, J=4 Hz); 2.45 (d, 2H, J=7 Hz); 1.87 (m, 1H); 1.65 (d, 3H, J=7 Hz); 0.97 (d, 6H, J=7 Hz).

(±)-1-(3-benzoylphenyl)ethane-N-methyl sulfonamide (44)

$^1$H-NMR (CDCl$_3$): δ 7.82 (d, 2H, J=7 Hz); 7.75 (s, 1H); 7.62 (d, 1H, J=7 Hz); 7.55 (m, 2H); 7.30 (m, 3H); 4.25 (bs, 1H, SO$_2$NH); 4.15 (m, 1H); 2.70 (d, 3H, J=4 Hz); 1.55 (d, 3H, J=7 Hz).

(±)-1-[4-(trifluoromethanesulfonyloxy)phenyl]ethane-N-methyl sulfonamide (45)

$^1$H-NMR (CDCl$_3$): δ 7.52 (d, 2H, J=7 Hz); 7.28 (d, 2H, J=7 Hz); 4.10 (bs, 1H, SO$_2$NH); 3.80 (m, 1H); 2.75 (d, 3H, J=4 Hz); 1.20 (d, 3H, J=7 Hz).

(±)-1-[4-(methanesulfonylamino)phenyl]ethane-N-methyl sulfonamide (46)

$^1$H-NMR (CDCl$_3$): δ 7.50 (d, 2H, J=7 Hz); 7.27 (d, 2H, J=7 Hz); 6.50 (bs, 1H, SO$_2$NH); 4.30 (bs, 1H, SO$_2$NR); 3.90 (m, 1H); 3.05 (s, 3H); 2.70 (d, 3H, J=4 Hz); 1.32 (d, 3H, J=7 Hz).

(±)-1-(4-isobutylphenyl)ethane-N-acetyl sulfonamide (47)

The compound has been synthesised, as above described, by acylation with acetyl chloride of the related 1-(4-isobutylphenyl)ethanesulfonamide.

$^1$H-NMR (CDCl$_3$): δ 7.28 (d, 2H, J=7 Hz); 7.20 (d, 2H, J=7 Hz); 4.82 (bs, 1H, SO$_2$NH); 4.30 (m, 1H); 2.45 (d, 2H, J=7 Hz); 1.85 (m, 1H); 1.80 (s, 3H); 1.65 (d, 3H, J=7 Hz); 0.97 (d, 6H, J=7 Hz).

EXAMPLE 6

General Procedure for the Synthesis of E/Z 2-aryl-2-methylethensulfonamides

A solution of the appropriate arylacetophenone (20 mmol) (prepared according to the above described method of general procedure for the synthesis of 1-arylethanesulfonic acids) in 10 mL of t-butyl alcohol is added dropwise over 20 min, to a commercial ylide, Iodomethylenetriphenylphosphorane (25 mmol), maintaining the reaction temperature below 25° C. and the resulting mixture is stirred for 4 h at room temperature. At the end of the reaction, the mixture is shaken with 50 ml of pentane and 50 ml of water, filtered, and the layers are separated. The aqueous layer is extracted with 3×50 ml of pentane and dried over sodium sulfate to afford, after purification by flash chromatography, the pure 2-(aryl) propene iodide (E/Z isomers mixture), (yield around 70%). The above Wittig olefination of a carbonyl compound has been utilized as described in Sotaro Miyano et al., Bull. Chem. Soc. J., 1197, 52 (1979).

The 2-(aryl) propene iodide (2 mmol) is dissolved in acetonitrile (5 mL) and is added to solution of potassium thioacecetate (4 mmol) in acetonitrile (2 ml) at room temperature; the reaction mixture is stirred for 4 hours. The mixture is quenced with water and extracted by EtOAc; the separated organic layers are dried, filtered and concentrated to give 2-arylpropenthioacetate (E/Z isomers mixture) (almost quantitative yield).

A solution of 2-aryl-2-methylethenthioacetate (1.00 mmol) in glacial acetic acid (2 mL) is stirred at 60° C. and treated dropwise with 30% $H_2O_2$ (4.56 mmol); the resulting solution is stirred at 60° C. for 24 hours, then the acetic acid is azeotropically removed with toluene. The residue is diluted with water (5 mL), neutralised with 1N NaOH, washed with diethyl ether (2×15 mL) and lyophilised to provide the 2-aryl-2-methylethenesulfonic acid sodium salt as E/Z isomers mixture as white solid (yield around 90%).

The E/Z 2-aryl-2-methylethensulfonamides are prepared according to the above described method of general procedure for the synthesis of E-arylethenesulfonamides to obtain E/Z-2-aryl-2-methyl-ethensulfonamides (0.75-0.85 mmol) (yield 85-95%) as colourless oils.

Following the above described procedure the following compounds have been synthesised:

E-2-(3-benzoylphenyl)-2-methyl ethenesulfonamide (48)
$^1$H-NMR (CDCl$_3$): δ 7.75 (m, 3H); 7.62 (m, 2H); 7.53 (m, 4H); 6.15 (d, 1H, J=1.4 Hz); 5.96 (d, 1H, J=1.3 Hz); 4.38 (bs, 2H, SONH$_2$); 2.10 (d, 3H, J=1.4 Hz); 2.0 (d, 3H, J=1.3 Hz).

E-2-(3-isopropylphenyl)-2-methyl ethenesulfonamide (49)
$^1$H-NMR (CDCl$_3$): δ 7.28 (m, 1H); 7.15 (m, 1H); 7.05 (m, 2H); 6.15 (d, 1H, J=1.4 Hz); 5.96 (d, 1H, J=1.3 Hz); 4.38 (bs, 2H, SONH$_2$); 3.15 (m, 1H); 2.10 (d, 3H, J=1.4 Hz); 2.0 (d, 3H, J=1.3 Hz); 1.25 (d, 6H, J=7 Hz).

E-2-(4isobutylphenyl)-2-methyl ethenesulfonamide (50)
$^1$H-NMR (CDCl$_3$): δ 7.32 (d, 2H, J=7 Hz); 7.23 (d, 2H, J=7 Hz); 6.15 (q, 1H, J=1.4 Hz); 5.96 (q, 1H, J=1.3 Hz); 4.35 (bs, 2H, SONH$_2$); 2.45 (d, 2H, J=7 Hz); 2.10 (d, 3H, J=1.4 Hz); 2.0 (d, 3H, J=1.3 Hz); 1.88 (m, 1H); 0.97 (d, 6H, J=7 Hz).

A list of chemical names and structures of the compounds in Examples 1-6 is reported in TABLE I.

TABLE I

| N. | NAME | STRUCTURE |
|---|---|---|
| 1 | (−)-1-(4-isobutylphenyl) ethanesulfonic acid sodium salt | 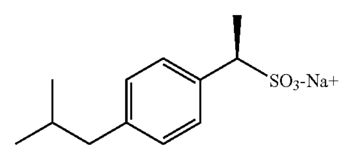 |
| 2 | (+)-1-(4-isobutylphenyl) ethanesulfonic acid sodium salt | 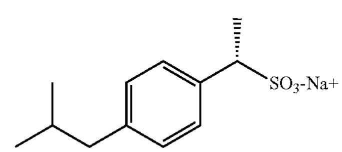 |
| 3 | (−)-1-[4-(1-oxo-2-isoindolinyl)phenyl] ethanesulfonic acid sodium salt | 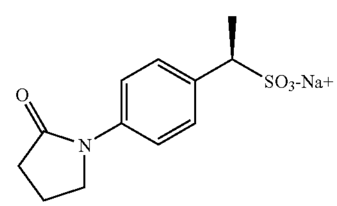 |
| 4 | (+)-1-[4-(1-oxo-2-isolndolinyl)phenyl] ethanesulfonic acid sodium salt | 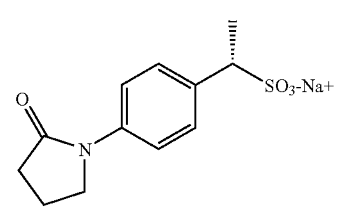 |

TABLE I-continued

| N. | NAME |
|---|---|
| 5 | (−)-2-(4-phenylsulfonyloxy) ethanesulfonic acid sodium salt |
| 6 | (+)-2-(4-phenylsulfonyloxy) ethanesulfonic acid sodium salt |
| 7 | (1-methyl-5-acetylpyrrolyl)-1-methanesulfonic acid sodium salt |
| 8 | (±)-2-(3-benzoylphenyl) ethanesulfonic acid sodium salt |
| 9 | (±)-2-(3-isopropylphenyl) ethanesulfonic acid sodium salt |
| 10 | E-2-(4-isobutylphenyl)ethenesulfonic acid sodium salt |
| 11 | E-2-(3-benzoylphenyl)ethenesulfonic acid sodium salt |
| 12 | E-2-(4-methanesulfonylaminophenyl) ethenesulfonic acid sodium salt |
| 13 | E-2-(4-trifluoromethanesulfonyloxy phenyl)ethenesulfonic acid sodium salt |
| 14 | E-2-(4-isobutylphenyl) ethenesulfonamide |

TABLE I-continued

| N. | NAME | STRUCTURE |
|---|---|---|
| 15 | E-2-(3-benzoylphenyl) ethenesulfonamide | 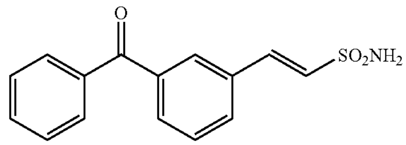 |
| 16 | E-2-[4-(trifluoromethanesulfonyloxy phenyl]ethenesulfonamide | 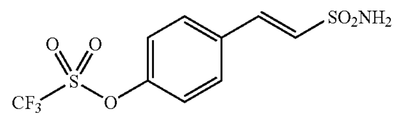 |
| 17 | E-2-[4-(methanesulfonylamino)phenyl] ethenesulfonamide | 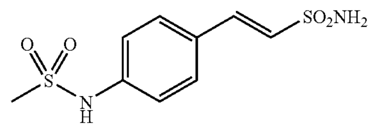 |
| 18 | E-2-(4-isobutylphenyl)ethene(N,N-dimethylaminopropyl) sulfonamide | 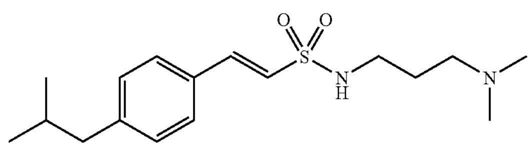 |
| 19 | E-2-(3-benzoylphenyl)etheneN-(N,N-dimethylaminopropyl) sulfonamide | 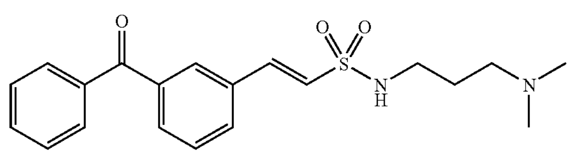 |
| 20 | E-2-[4-(trifluoromethanesulfonyloxy) phenyl]ethene-(N,N-dimethylamino propyl)sulfonamide | 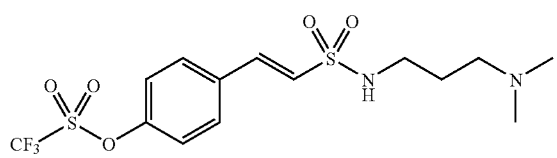 |
| 21 | E-2-[4-(methanesulfonylamino)phenyl] ethene-(N,N-dimethylaminopropyl) sulfonamide | 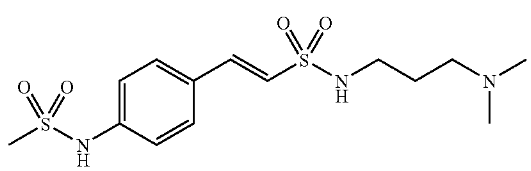 |
| 22 | E-2-(4-isobutylphenyl)ethene-N-methyl sulfonamide | 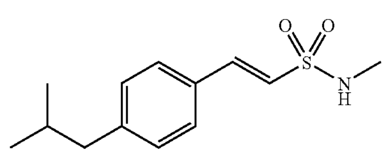 |
| 23 | E-2-(3-benoylphenyl)ethene-N-methyl sulfonamide | 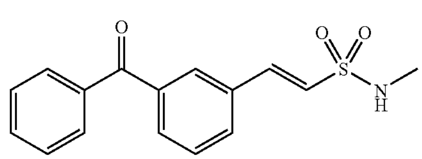 |
| 24 | E-2-[4-(trifluoromethanesulfonyloxy) phenyl]ethene-N-methyl sulfonamide | 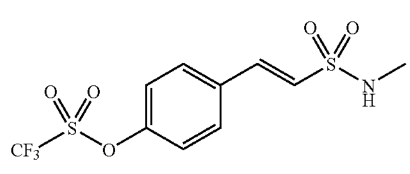 |

TABLE I-continued

| N. | NAME | STRUCTURE |
|---|---|---|
| 25 | E-2-[4-(methanesulfonylamino)phenyl] ethene-N-methyl sulfonamide | 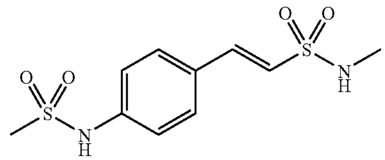 |
| 26 | E-2-(4-isobutylphenyl)ethene-N-(2-methoxyethyl) sulfonamide | 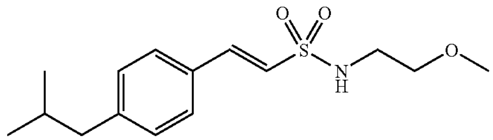 |
| 27 | E-2-(3-benzoylphenyl)ethene-N-(2-methoxyethyl) sulfonamide | 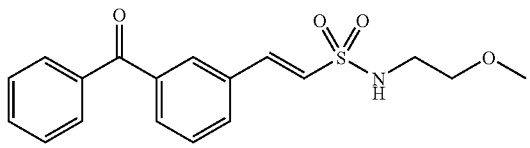 |
| 28 | E-2-[4-(trifluoromethanesulfonyloxy)phenyl]ethen-N-(2-methoxyethyl) sulfonamide | 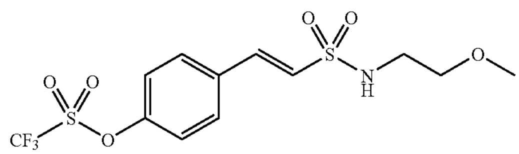 |
| 29 | E-2-[4-(methanesulfonylamino) phenyl]ethen-N-(2-methoxyethyl) sulfonamide | 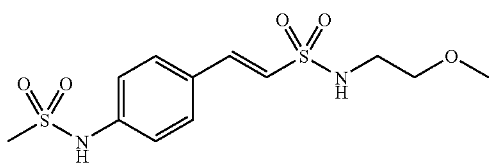 |
| 30 | (1-methyl-5-isobutirrylpyrrolyl)-1-methanesulfonamide | 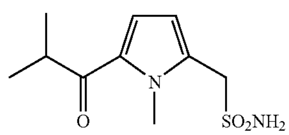 |
| 31 | (1-methyl-5-acetylpyrrolyl)-1-methanesulfonamide | 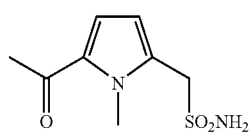 |
| 32 | (−)-1-(4-isobutylphenyl)ethane sulfonamide | 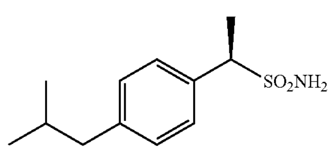 |
| 33 | (+)-1-(4-isobutylphenyl)ethane sulfonamide | 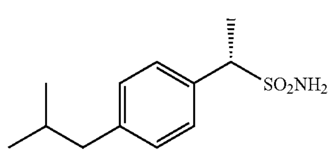 |
| 34 | (+)-1-(3-isopropylphenyl)ethane sulfonamide | 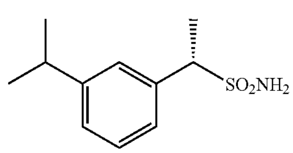 |

TABLE I-continued

| N. | NAME | STRUCTURE |
|---|---|---|
| 35 | (±)-1-(4-isobutylphenyl)ethane-N-(N,N-dimethylaminopropyl) sulfonamide | 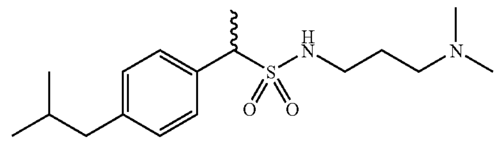 |
| 36 | (±)-1-(3-benzoylphenyl)ethane-N-(N,N-dimethylaminopropyl) sulfonamide | 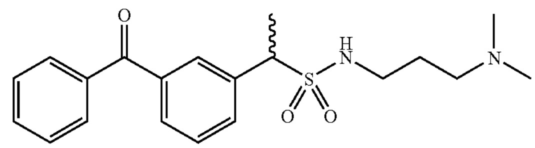 |
| 37 | (±)-1-(4-(trifluoromethanesulfonyloxy) phenyl]ethane-N-(N,N-dimethylaminopropyl) sulfonamide | 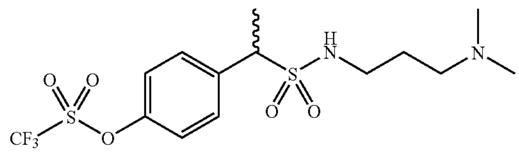 |
| 38 | (±)1-[4-(methanesulfonylamino) phenyl]ethane-N-(N,N-dimethylaminopropyl) sulfonamide | 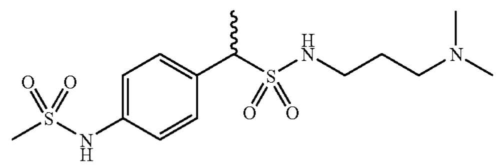 |
| 39 | (±)-1-(4-isobutylphenyl)ethane-N-(2-methoxyethyl) sulfonamide | 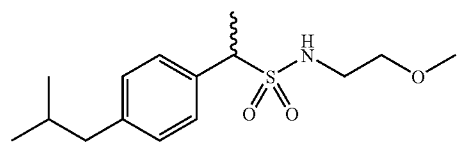 |
| 40 | (±)-1-(3-benzoylphenyl)ethane-N-(2-methoxyethyl) sulfonamide | 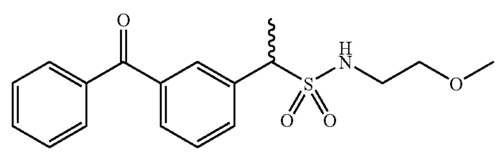 |
| 41 | (±)-1-[4-(trifluoromethanesulfonyloxy) phenyl]ethane-N-(2-methoxyethyl) sulfonamide | 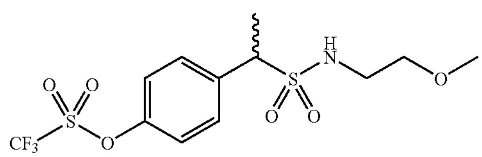 |
| 42 | (±)-1-[4-(methanesulfonylamino) phenyl]ethane-N-(2-methoxyethyl) sulfonamide | 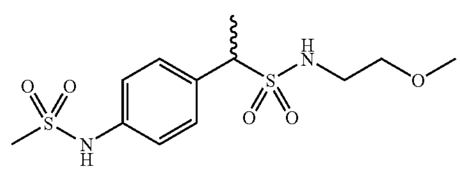 |
| 43 | (±)-1-(4-isobutylphenyl)ethane-N-methyl sulfonamide | 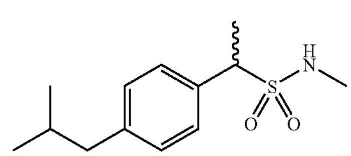 |

TABLE I-continued

| N. | NAME | STRUCTURE |
|---|---|---|
| 44 | (±)-1-(3-benzoylphenyl)ethane-N-methyl sulfonamide | 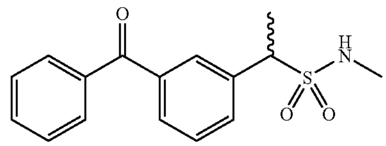 |
| 45 | (±)-1-[4-(trifluoromethanesulfonyloxy) phenyl]ethane-N-methyl sulfonamide | 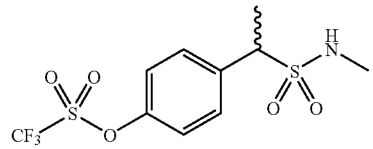 |
| 46 | (±)-1-[4-(methanesulfonylamino) phenyl]ethane-N-methyl sulfonamide | 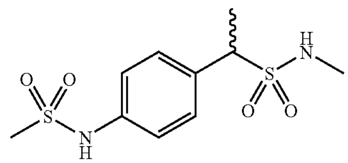 |
| 47 | (±)-1-(4-isobutylphenyl)ethane-N-acetyl sulfonamide | 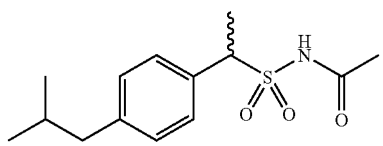 |
| 48 | E-2-(3-benzoylphenyl)-2-methyl-ethenesulfonamide | 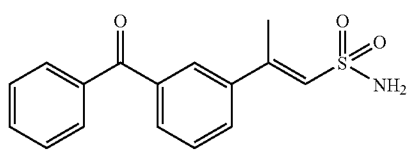 |
| 49 | E-2-(3-isopropylphenyl)-2-methyl-ethenesulfonamide | 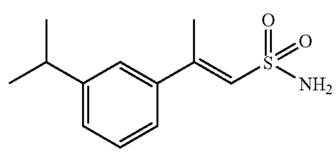 |
| 50 | E-2-(4-isobutylphenyl)-2-methyl-ethenesulfonamide | 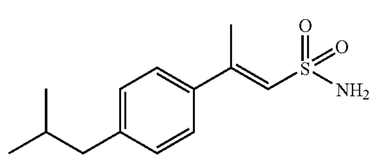 |

TABLE II

Inhibition (%) of human PMNs chemotaxis induced by IL-8 (100 ng/mL)

| N. | IL-8 PMN chemotaxis inhibition % ($c = 10^{-8}$) | STRUCTURE |
|---|---|---|
| 1 | 55 ± 7 | 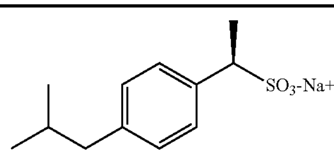 |

TABLE II-continued

Inhibition (%) of human PMNs chemotaxis induced by IL-8 (100 ng/mL)

| N. | IL-8 PMN chemotaxis inhibition % (c = $10^{-8}$) | STRUCTURE |
|---|---|---|
| 2 | 35 ± 7 | (4-isobutylphenyl)-CH(CH₃)-SO₃⁻Na⁺ |
| 7 | 35 ± 2 | 2-acetyl-1-methyl-5-(CH₂SO₃⁻Na⁺)-pyrrole |
| 8 | 65 ± 4 | 3-benzoylphenyl-CH(-)-SO₃⁻Na⁺ |
| 10 | 45 ± 4 | (E)-(4-isobutylphenyl)-CH=CH-SO₃⁻Na⁺ |
| 14 | 41 ± 17 | (E)-(4-isobutylphenyl)-CH=CH-SO₂NH₂ |
| 15 | 66 ± 10 | (E)-(3-benzoylphenyl)-CH=CH-SO₂NH₂ |
| 17 | 41 ± 17* | (E)-[4-(methylsulfonylamino)phenyl]-CH=CH-SO₂NH₂ |
| 18 | 40 ± 1 | (E)-(4-isobutylphenyl)-CH=CH-SO₂NH-(CH₂)₃-N(CH₃)₂ |
| 20 | 60 ± 1 | (E)-[4-(trifluoromethylsulfonyloxy)phenyl]-CH=CH-SO₂NH-(CH₂)₃-N(CH₃)₂ |
| 21 | 31 ± 6 | (E)-[4-(methylsulfonylamino)phenyl]-CH=CH-SO₂NH-(CH₂)₃-N(CH₃)₂ |

TABLE II-continued

Inhibition (%) of human PMNs chemotaxis induced by IL-8 (100 ng/mL)

| N. | IL-8 PMN chemotaxis inhibition % (c = $10^{-8}$) | STRUCTURE |
|----|----|----|
| 22 | 41 ± 9* | 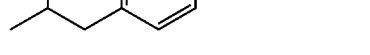 |
| 26 | 50 ± 4* | 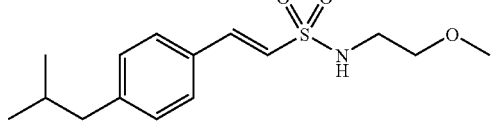 |
| 30 | 50 ± 1 | 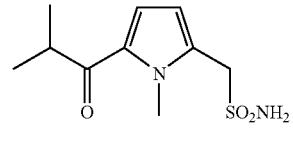 |
| 31 | 39 ± 4 | 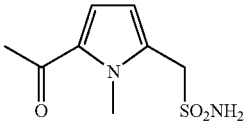 |
| 36 | 49 ± 14 | 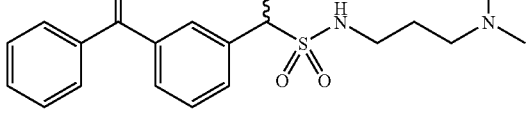 |
| 43 | 36 ± 15* | 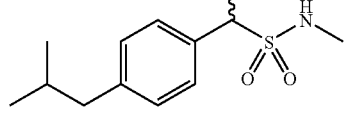 |
| 47 | 40 ± 17 | 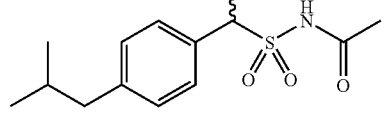 |
| 50 | 32 ± 1 | 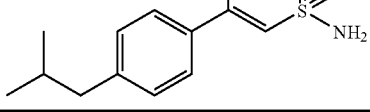 |

*compounds were tested at c = $10^{-7}$

The invention claimed is:

1. A compound of formula (I):

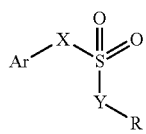

and pharmaceutically acceptable salts thereof, wherein

Ar is a substituted phenyl group, selected from 3'-benzoylphenyl, 3'-(4-chloro-benzoyl)-phenyl, 3'-(4-methyl-benzoyl)-phenyl, 3'-acetyl-phenyl, 3'-propionyl-phenyl, 3'-isobutanoyl-phenyl, 4'-trifluoromethanesulfonyloxy-phenyl, 4'-benzenesulfonyloxy-phenyl, 4'-trifluoromethanesulfonylamino-phenyl, 4'-benzenesulfonylamino-phenyl, 4'-benzenesulfonylmethyl-phenyl, 4'-acetoxyphenyl, 4'-propionyloxy-phenyl, 4'-benzoyloxy-phenyl, 4'acetylamino-phenyl, 4'propionylamino-phenyl, 4'-benzoylamino-phenyl, or Ar is a substituted 5-6 membered heteroaryl ring;

X represents either a —CH$_2$— or a —CH(CH$_3$)— group or an ethylenic group of formula (II)

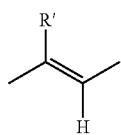

in the E configuration wherein R' is hydrogen (H) or CH$_3$;
Y is selected from oxygen (O) and NH; and
when Y is O, R is H;
when Y is NH, R is selected from H, C$_1$-C$_5$-alkyl, C$_1$-C$_5$-cycloalkyl, C$_1$-C$_5$-alkenyl, C$_1$-C$_5$-acyl, a residue of formula —CH$_2$—CH$_2$—Z—(CH$_2$—CH$_2$O)nR" wherein R" is H or C$_1$-C$_5$-alkyl, n is an integer from 0 to 2 and Z is oxygen or sulfur, a residue of formula —(CH2)n-NRaRb wherein n is an integer from 0 to 5 and each Ra and Rb, which may be the same or different, are C$_1$-C$_6$-alkyl, C$_1$-C$_6$-alkenyl or Ra and Rb, together with the nitrogen atom to which they are bound, form a heterocycle from 3 to 7 members of formula (III)

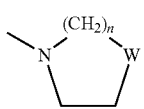

wherein W represents a single bond, CH2, O, S or N-Rc, Rc being H, C$_1$-C$_6$-alkyl or C$_1$-C$_6$-alkylphenyl.

2. The compound according to claim 1, wherein Ar is a heteroaryl ring selected from substituted pyridine, pyrrole, thiophene, furane, or indole.

3. The compound according to claim 1, wherein YR is OH.

4. The compound according to claim 1, wherein Y is NH and R is:
H, C$_1$-C$_5$ alkyl, C$_1$-C$_5$ acyl;
a residue of formula —CH$_2$—CH$_2$—O—(CH$_2$—CH$_2$O)R" wherein R" is H or C$_1$-C$_5$-alkyl;
a residue of formula —(CH2)n-NRaRb wherein n is the integer 2 or 3, more preferably 3 and the group NRaRb is N,N-dimethylamine, N,N-diethylamine, 1-piperidyl, 4-morpholyl, 1-pyrrolidyl, 1-piperazinyl, 1-(4-methyl) piperazinyl.

5. The compound of claim 1, selected from the group consisting of:
1-(4-isobutylphenyl)ethanesulfonic acid
1-[4-(1-oxo-2-isoindolinyl)phenyl]ethanesulfonic acid
2-(4-phenylsulfonyloxy)ethanesulfonic acid
(1-methyl-5-acetylpyrrolyl)-1-methanesulfonic acid
2-(3-benzoylphenyl)ethanesulfonic acid
2-(3-isopropylphenyl)ethanesulfonic acid
E-2-(4-isobutylphenyl)ethenesulfonic acid
E-2-(3-benzoylphenyl)ethenesulfonic acid
E-2-(4-methanesulfonylaminophenyl)ethenesulfonic acid
E-2-(4-trifluoromethanesulfonyloxyphenyl)ethenesulfonic acid
E-2-(4-isobutylphenyl)ethenesulfonamide
E-2-(3-benzoylphenyl)ethenesulfonamide
E-2-[4-(trifluoromethanesulfonyloxy)phenyl]ethenesulfonamide
E-2-[4-(methanesulfonylamino)phenyl]ethenesulfonamide
E-2-(4-isobutylphenyl)ethene-N-(N,N-dimethylaminopropyl)sulfonamide
E-2-(3-benzoylphenyl)ethene-N-(N,N-dimethylaminopropyl)sulfonamide
E-2-[4(trifluoromethanesulfonyloxy)phenyl]ethene-N-(N,N-dimethylaminopropyl) sulfonamide
E-2-[4-(methanesulfonylamino)phenyl]ethene-N-(N,N-dimethylaminopropyl)sulfonamide
E-2-(4-isobutylphenyl)ethene-N-methyl sulfonamide
E-2-(3-benzoylphenyl)ethene-N-methyl sulfonamide
E-2-[4-(trifluoromethanesulfonyloxy)phenyl]ethene-N-methyl sulfonamide
E-2-[4-(methanesulfonylamino)phenyl]ethene-N-methyl sulfonamide
E-2-(4-isobutylphenyl)ethene-N-(2"-methoxyethyl)sulfonamide
E-2-(3-benzoylphenyl)ethene-N-(2"-methoxyethyl)sulfonamide
E-2-[4-(trifluoromethanesulfonyloxy)phenyl]ethene-N-(2"-methoxyethyl)sulfonamide
E-2-[4-(methanesulfonylamino)phenyl]ethene-N-(2"-methoxyethyl)sulfonamide
(1-methyl-5-isobutirrylpyrrolyl)-1-methanesulfonamide
(1-methyl-5-acetylpyrrolyl)-1-methanesulfonamide
1-(4-isobutylphenyl)ethanesulfonamide
1-(3-isopropylphenyl)ethanesulfonamide
1-(4-isobutylphenyl)ethane-N-(N,N-dimethylaminopropyl)sulfonamide
1-(3-benzoylphenyl)ethane-N-(N,N-dimethylaminopropyl)sulfonamide
1-[4-(trifluoromethanesulfonyloxy)phenyl]ethane-N-(N,N-dimethylaminopropyl) sulfonamide
1-[4-(methanesulfonylamino)phenyl]ethane-N-(N,N-dimethylaminopropyl)sulfonamide
1-(4-isobutylphenyl)ethane-N-(2-methoxyethyl)sulfonamide
1-(3-benzoylphenyl)ethane-N-(2-methoxyethyl)sulfonamide
1-[4-(trifluoromethanesulfonyloxy)phenyl]ethane-N-(2-methoxyethyl)sulfonamide
1-[4-(methanesulfonylamino)phenyl]ethane-N-(2-methoxyethyl)sulfonamide
1-(4-isobutylphenyl)ethane-N-methyl sulfonamide
1-(3-benzoylphenyl)ethane-N-methyl sulfonamide
1-[4-(trifluoromethanesulfonyloxy)phenyl]ethane-N-methyl sulfonamide
1-[4-(methanesulfonylamino)phenyl]ethane-N-methyl sulfonamide
1-[4-isobutylphenyl]ethane-N-acetyl sulfonamide
E-2-(3-benzoylphenyl)-2-methyl-ethenesulfonamide
E-2-(3-isopropylphenyl)-2-methyl-ethenesulfonamide
E-2-(4-isobutylphenyl)-2-methyl-ethenesulfonamide
and pharmaceutically acceptable salts thereof.

6. Compounds according to claim 5, wherein the compounds are ethanesulfonamides, in the form of single (−) or (+) enantiomers.

7. A method for inhibiting chemotaxis of human polymorphonuclear lymphocytes induced by IL-8 which comprises administering to an individual in need thereof an effective amount of a compound of formula (I):

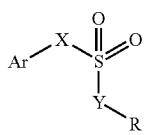

(I)

or a pharmaceutically acceptable salts thereof,
wherein
Ar is a substituted phenyl group selected from the group consisting of 3'-benzoylphenyl, 3'-(4-chloro-benzoyl)-phenyl, 3'-(4-methyl-benzoyl)-phenyl, 3'-acetyl-phenyl, 3'-propionyl-phenyl, 3'-isobutanoyl-phenyl, 4'-trifluoromethanesulfonyloxy-phenyl, 4'-benzenesulfonyloxy-phenyl, 4'-trifluoromethanesulfonylamino-phenyl, 4'-benzenesulfonylamino-phenyl, 4'-benzenesulfonylmethyl-phenyl, 4'-acetoxyphenyl, 4'-propionyloxy-phenyl, 4-benzoyloxy-phenyl, 4'acetylamino-phenyl, 4'propionylamino-phenyl, 4'-benzoylamino-phenyl, or a heteroaryl ring selected from the group consisting of pyridine, pyrrole, thiophene, furane and indole;
X represents —$CH_2$—, —$CH(CH_3)$— or an ethylenic group of formula (II)

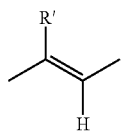

(II)

in the E configuration wherein R' is hydrogen (H) or $CH_3$;
Y is selected from oxygen (O) and NH; and
when Y is O, R is H;
when Y is NH, R is selected from the group consisting of H, $C_1$-$C_5$-alkyl, $C_1$-$C_5$cycloalkyl, $C_1$-$C_5$-alkenyl, $C_1$-$C_5$-acyl, a residue of formula —$CH_2$—$CH_2$—Z—($CH_2$—$CH_2$O)nR" wherein R" is H or $C_1$-$C_5$ alkyl, n is an integer from 0 to 2 and Z is O or sulfur (S), or a residue of formula —($CH_2$)n-NRaRb wherein n is an integer from 0 to 5 and each Ra and Rb, which may be the same or different, are $C_1$-$C_6$-alkyl, $C_1$-$C_6$-alkenyl or Ra and Rb, together with the nitrogen atom to which they are bound, form a heterocycle from 3 to 7 members of formula (III)

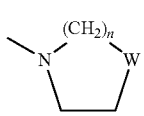

(III)

wherein W represents a single bond, $CH_2$, O, S or N-Rc, Rc being H, $C_1$-$C_6$-alkyl or $C_1$-$C_6$-alkylphenyl.

8. The method according to claim 7 wherein the individual is treated for psoriasis, ulcerative colitis, melanoma, chronic obstructive pulmonary disease (COPD), bullous pemphigoid, rheumatoid arthritis, idiopathic fibrosis, glomerulonephritis or for the treatment of damage caused by ischemia and reperfusion.

9. The method according to claim 7, wherein YR is OH.

10. The method according to claim 7, wherein Y is NH and R is:
H, $C_1$-$C_5$ alkyl, $C_1$-$C_5$ acyl, a residue of formula —$CH_2$—$CH_2$—O—($CH_2$—$CH_2$O)R" wherein R" is H or $C_1$-$C_5$-alkyl, or a residue of formula —(CH2)n-NRaRb wherein n is the integer 2 or 3 and the group NRaRb is N,N-dimethylamine, N,N-diethylamine, 1-piperidyl, 4-morpholyl, 1-pyrrolidyl, 1-piperazinyl or 1-(4-methyl)piperazinyl.

11. The method according to claim 7 wherein said compound of formula (I) is selected from:
1-(4-isobutylphenyl)ethanesulfonic acid,
1[4-(1-oxo-2-isoindolinyl)phenyl]ethanesulfonic acid,
2-(4-phenylsulfonyloxy)ethanesulfonic acid,
(1-methyl-5-acetylpyrrolyl)-1-methanesulfonic acid,
2-(3-benzoylphenyl)ethanesulfonic acid,
2-(3-isopropylphenyl)ethanesulfonic acid,
E-2-(4-isobutylphenyl)ethenesulfonic acid,
E-2-(3-benzoylphenyl)ethenesulfonic acid,
E-2-(4-methanesulfonylaminophenyl)ethenesulfonic acid,
E-2-(4-trifluoromethanesulfonyloxyphenyl)ethenesulfonic acid,
E-2-(4-isobutylphenyl)ethenesulfonamide,
E-2-(3-benzoylphenyl)ethenesulfonamide,
E-2-[4-(trifluoromethanesulfonyloxy)phenyl]ethenesulfonamide,
E-2-[4-(methanesulfonylamino)phenyl]ethenesulfonamide,
E-2-(4-isobutylphenyl)ethene-N-(N,N-dimethylaminopropyl)sulfonamide,
E-2-(3-benzoylphenyl)ethene-N-(N,N-dimethylaminopropyl)sulfonamide,
E-2-[4-(trifluoromethanesulfonyloxy)phenyl]ethene-N-(N,N-dimethylaminopropyl) sulfonamide,
E-2-[4-(methanesulfonylamino)phenyl]ethene-N-(N,N-dimethylaminopropyl) sulfonamide,
E-2-(4-isobutylphenyl)ethene-N-methyl sulfonamide,
E-2-(3-benzoylphenyl)ethene-N-methyl sulfonamide,
E-2-[4-(trifluoromethanesulfonyloxy)phenyl]ethene-N-methyl sulfonamide,
E-2-[4-(methanesulfonylamino)phenyl]ethene-N-methyl sulfonamide,
E-2-(4-isobutylphenyl)ethene-N-(2"-methoxyethyl)sulfonamide,
E-2-(3-benzoylphenyl)ethene-N-(2"-methoxyethyl)sulfonamide,
E-2-[4-(trifluoromethanesulfonyloxy)phenyl]ethene-N-(2"-methoxyethyl)sulfonamide,
E-2-[4-(methanesulfonylamino)phenyl]ethene-N-(2"-methoxyethyl)sulfonamide,
(1-methyl-5-isobutirrylpyrrolyl)-1-methanesulfonamide,
(1-methyl -5-acetylpyrrolyl)-1-methanesulfonamide,
1-(4-isobutylphenyl)ethanesulfonamide,
1-(3-isopropylphenyl)ethanesulfonamide,
1-(4-isobutylphenyl)ethane-N-(N,N-dimethylaminopropyl)sulfonamide,
1-(3-benzoylphenyl)ethane-N-(N,N-dimethylaminopropyl)sulfonamide,
1-[4-(trifluoromethanesulfonyloxy)phenyl]ethane-N-(N,N-dimethylaminopropyl) sulfonamide,
1-[4-(methanesulfonylamino)phenyl]ethane-N-(N,N-dimethylaminopropyl) sulfonamide,
1-(4-isobutylphenyl)ethane-N-(2-methoxyethyl)sulfonamide,
1-(3-benzoylphenyl)ethane-N-(2-methoxyethyl)sulfonamide, 1-[4-(trifluoromethanesulfonyloxy)phenyl]ethane-N-(2-methoxyethyl)sulfonamide,
1-[4-(methanesulfonylamino)phenyl]ethane-N-(2-methoxyethyl)sulfonamide,
1-(4-isobutylphenyl)ethane-N-methyl sulfonamide,
1-(3-benzoylphenyl)ethane-N-methyl sulfonamide,
1-[4-(trifluoromethanesulfonyloxy)phenyl]ethane-N-methyl sulfonamide,
1-[4(methanesulfonylamino)phenyl]ethane-N-methyl sulfonamide,
1-[4-isobutylphenyl]ethane-N-acetyl sulfonamide,
E-2-(3-benzoylphenyl)-2-methyl-ethenesulfonamide,
E-2-(3-isopropylphenyl)-2-methyl-ethenesulfonamide,
E-2-(4-isobutylphenyl)-2-methyl-ethenesulfonamide,
and pharmaceutically acceptable salts thereof.

12. The method according to claim 11, wherein the compounds are ethanesulphonamides in the form of single(−) or (+) enantiomers.

* * * * *